United States Patent
Sze et al.

(10) Patent No.: US 7,993,926 B2
(45) Date of Patent: Aug. 9, 2011

(54) GUARD CELL-SPECIFIC TOOL FOR MOLECULAR MANIPULATION OF DROUGHT AVOIDANCE/WATER LOSS IN PLANTS

(75) Inventors: Heven Sze, Beltsville, MD (US); Senthilkumar Padmanaban, Greenbelt, MD (US); June Kwak, North Potomac, MD (US)

(73) Assignee: University of Maryland, College Park, College Park, MD (US)

( * ) Notice: Subject to any disclaimer, the term of this patent is extended or adjusted under 35 U.S.C. 154(b) by 84 days.

(21) Appl. No.: 11/798,624

(22) Filed: May 15, 2007

(65) Prior Publication Data

US 2008/0028489 A1   Jan. 31, 2008

Related U.S. Application Data

(60) Provisional application No. 60/747,239, filed on May 15, 2006.

(51) Int. Cl.
*A01H 5/00* (2006.01)
*C12N 15/82* (2006.01)
*C07H 21/00* (2006.01)

(52) U.S. Cl. .................... 435/468; 435/320.1; 536/24.1; 800/287

(58) Field of Classification Search .................... None
See application file for complete search history.

(56) References Cited

FOREIGN PATENT DOCUMENTS

EP    1111051    *    6/2001

OTHER PUBLICATIONS

Padmanaban et al., Plant Physiology, 2007, vol. 144, pp. 82-93.*
Choisne et al., GenBank Acc. No. AL132960, Apr. 16, 2005.*
Ichide et al., Plant Cell, 1999, vol. 9, pp. 1843-1857.*

* cited by examiner

*Primary Examiner* — Ashwin Mehta

(57) ABSTRACT

The inventors herein disclose a new transporter that participates in guard cell movement. The inventors have now found that AtCHX20 is preferentially expressed in guard cells using microarray and promoter TGUS analyses. The inventors have also found a guard cell specific promoter which serves as a powerful tool to manipulate the opening and closing of guard cells and thus the ability to control water loss and gas exchange of plants. Such a tool can be particularly useful when applied to crops and other plants of economic importance, thus the present inventors have identified homologous genes in several other plants that fall within the scope of this invention.

26 Claims, 22 Drawing Sheets

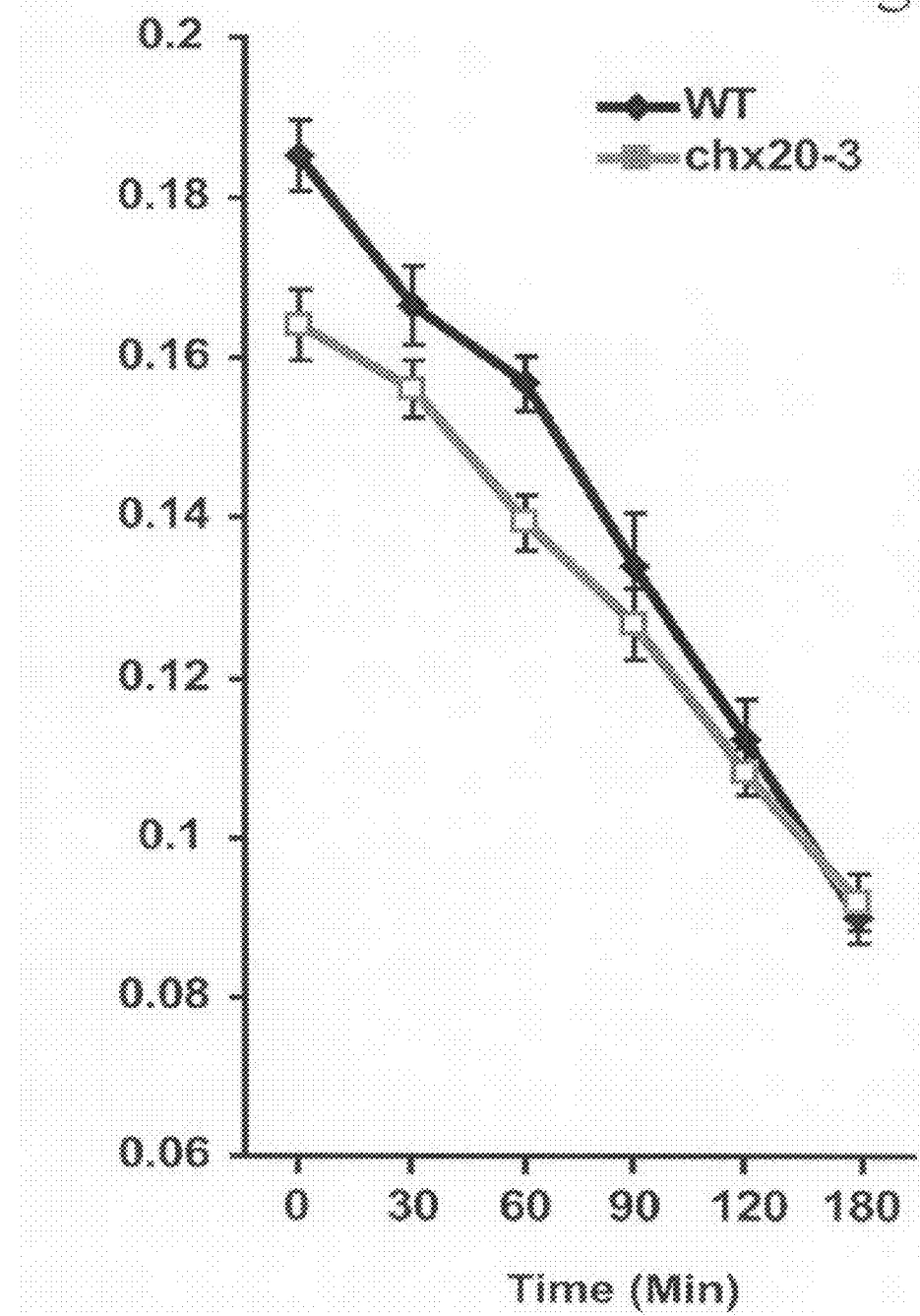

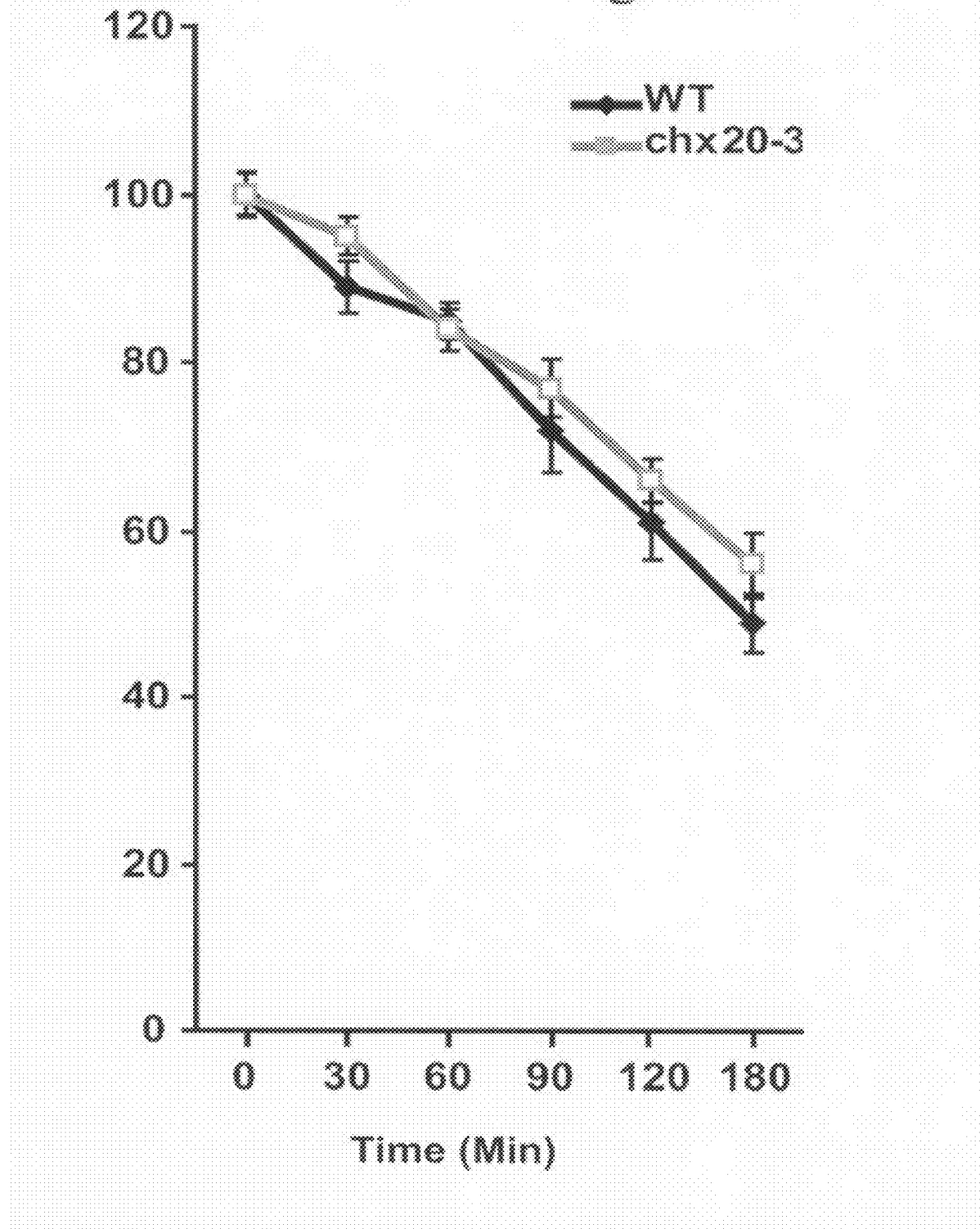

```
AtCHX20  MPFNITSVKTSSNGVTQGDNPLNFA----FPLLIVQTALIIAVSRFIAVLEKPLRQFKVIAEIVGGILLGPSALGRMMAYMDRIFFKWSMPILESVASIG    96
ScKHA1   ------MANTVGGILSGVNPFHYNSSSPLITLFLFQACLILLVCNLIHIPFSMMRQPKVISEVISGVILGPTIFGQIPNYTNTIFFTSSIPGIALVANLG    93
         : . :**    . :*:       *: *: : .    : . ::. * ::*:. :. : .:   :* . :: . *:* .:*:*** :**:**:.::.:*

AtCHX20  LLFLFLVGLELDLSSIRRSGKRAFGIAVAGITLPFTAGVGVAFVIRNTLYTAADKP---GYAEFLVFMGVALSITAFFVLARIIAELKLLTTQIGETAM   193
ScKHA1   ILLEMFFLGLEVDIAFTIKKHLEKRALVIGIVTLAVPFGFGCLLAIPLFFTYANKTEGERHIKFSVEMVFIAVSISVTAFFVLCRIIANELRLIKDRAGIVVL   193
         :* *::.** :*::   ::::.  : .:*. *  *.   . *  *::  .::*     . . *::.. :   :.*.*:***** :*::**::.  ::

AtCHX20  AAAAFNDVAANILLALAVALAGNGEGGEGGEKKSPLVSLMVLLSGAGEVVFMLVVIRPGMWVAKRGSPENDVVRESYVCLTLAGVM--VSGFASDLIGHES   292
ScKHA1   AAGINDIMGFILLALSIISSAEG-------SPVNTVYILLITFANFLIYFFPLXYLLAYH-----RGTHRKLKDLSASQDSTKEEL-----------------   286
         **. :*:  .:**** :  :          *: .:::*: *  *    : :.:  :      :* :.:. .

AtCHX20  IFGAFVFGLTIPDGEFGQRLIERIEDFVSGLLLPLYFATSGLKTDVAKIRGAESWEMLGLVVTACAGRKTVGFYVAVMVKVPAREALTLGFLMNTKGL   392
ScKHA1   IFGAFIAGLVVFFDDHVVKLTERMEDIFNIVFIPLYFAVAGLAVDLTLLANEGRDWGYVFAFIGIAIPFTKIISGTLTAKLYGLLFREATAAGVLMSCKGI   386
         ****: **. :   .. ::  **: *:.  . :****.:.** .*::: .... . .. :. :       :*. : ::*: :   :* :.  .* *

AtCHX20  VELIVLNIGKEKKVLNDETFALIVMLMALFTFITFPTMAIYKPA-RGTHRKLKDLSASQDSTKEEL---------RILACLEGPANVSS----LISIVESIR   481
ScKHA1   VEIVVLTVGLNAGIISRKIFGMFVLMALVSTFVFTFPLTQLVFPDSYRDGVKKSLSTPAEDDGAADGLDSEGVDKTEINTQLNSLADVSKYRIGELTVIN   486
         **:*.*.:*  : :.:  *.: :::**. ***  :**   :        :.:  * *: .  :        .:  : .: . ..*   :*.   .
```

Fig. 9A

```
AtCHX20  TTKILRLKLFVMHLMEL----------TERSSSIIMVQRARKNGLPFVERYRHGERHSNVIGGFEAYRQLGRVAVRPITAVSPLPTMHEDICHMAD 567
ScKHA1   TTEAISPSLKLIAVTLSLGVSPKPANMKHRNEFSLSRMTATDSTLRSNTFKIKNAVH--IWSKSVDDVDFNLSVIDEKLTPFEGVGALRAIHLRLLTERT 584
         **:  * :::  *:     :   ::: ::   *    * :   *:   **  . . :  :*: .  : :* :*: *:.:  * : .::  :

AtCHX20  TKRVTMIILPFHKRKNADEGHSHHHQDGGDGNVPENVGEGMRLIVNQRVLKNAPCSVAVLVDRGLGSIEAQTLSLDGSNVVERVCVIP----FGGFDDRE 663
ScKHA1   TD-----LLQSSSLTRDDPHFTANTDSLLQIFDIFSNLSK-IPFSSEVIFSTMREKAANIATMMDSTDJLLLPLKGASYEYRGSPVFIDEKYANPDHIY 678
         *:      *  ..*  : . . * : *:: :  *:  **   *:*: **: * :..    : : :*.  :.:***:*..  *: **:   *:. .

AtCHX20  SIELGGRMAEHPAVRVTVIRFLVRETLRSTAVTLRPAPSKGKERNYAFLITNVDPEKEKELDEGALEDFKSKMKEMVBYKERE--PNNIEEILSIGQSK 761
ScKHA1   SHLLGLNELSSTFFYKSIFQSLRANFAVQISNTYGRLANDRFKRKRSTLL----LPKPYLVQSPDYIGLYLLLLICYRDGYNNDNASCGSIFNSRNIDFAK 773
         * : *  :   .  :   :: :* . *..::  * *..: :. :*:.: **      ..:  .*:*:* *: **.::.:  : .. :*.... : :*

AtCHX20  DFDLIVVERGRIPSAEVVAALAEHQAEHPELGPIG----------DVLASSIDHIIPSILVVQQEN--KAHVEDITVSKITVSESSLSINGDTNV----- 842
ScKHA1   DLSTAPAHDMLANESTKIVDIPETRVPEEAIERPSFTEVLDVGLSPDTALADIEETTFIIGEDLPDESEPFSEEVRVTFEGSNREDTLIVHEPSSE 873
         * .  .  .:   .  ..    . :  .*. :*       ::   :**    .:::.   : *  ..  .:* :  * .:   .*:  .

| Organism | Locus | Gene Name | BAC Clone | Position | cDNA (bp) | bp | Protein | aa |
|---|---|---|---|---|---|---|---|---|
| A. thaliana | At3g53720 | AtCHX20 | AL132960 | [-] 12,536-8,335 | BT002529 | 2762 | AA000889 | 842 |
| O. sativa | Os05g02240 or Os05g0113300 | OsCHX12 | AC093921 | 25,581-29,615 | AK106443 | 2781 | BAF16369 | 844 |
| M. truncatula | MtrDRAFT_AC148343g6v2 | MtCHX20 (putative) | AC148343 | 23,653-29,660 | AC148343_6.2 | 2802 | ABD32190 | 851 |
| P. trichocarpa | Poptr1/LG_VI:3721780-3726777 | fgenesh1_pg.C_LG_VI000480 | n/a | n/a | n/a | n/a | n/a | 812 |
| Z. mays | 19577.t000001 | 19577.m000012 | n/a | n/a | n/a | n/a | n/a | 785 |

| Organism | 5' Neighbor | direction | 3' Neighbor | direction | Promoter Region* |
|---|---|---|---|---|---|
| A. thaliana | At3g53730 | same | At3g53710 | same | 2632 |
| O. sativa | Os05g02230 | same | Os05g02250 | same | 4172 |
| M. truncatula | MtrDRAFT_AC148343g18v2 | same | MtrDRAFT_AC148343g7v2 | same | 678 |
| P. trichocarpa | estExt_fgenesh1_pg_v1.C_LG_VI1515 | same | fgenesh1_pg.C_LG_VI000481 | same | 10708 |
| Z. mays | | | | | |

* Region defined as that which is between ATG of gene and ATG or STOP of 5' neighbor gene.

Websites used to find neighbor genes:

At = SIGnAL "T-DNA Express" Arabidopsis Gene Mapping Tool (http://signal.salk.edu/cgi-bin/tdnaexpress)
Os = RiceGE : Rice Functional Genomics Database (http://signal.salk.edu/cgi-bin/RiceGE)
Mt = BAC clone (5' neighbor might not be real; if you take this out, promoter region is 2218)
Pt = http://genome.jgi-psf.org/Poptr1/Poptr1.home.html
Zm = TIGR Maize Genome Broswer (http://www.tigr.org/tigr-scripts/gbrowse/gbrowse/zma1/)

GUARD CELL-SPECIFIC TOOL FOR MOLECULAR MANIPULATION OF DROUGHT AVOIDANCE/WATER LOSS IN PLANTS

CROSS-REFERENCE TO RELATED APPLICATIONS

This application claims priority to U.S. provisional patent application Ser. No. 60/747,239, filed May 15, 2006, and incorporated herein as if set forth in its entirety.

This invention was made with U.S. Government support under National Science Foundation grant IBN0209788 and MCB-0614203. The U.S. Government retains certain rights to this invention.

BACKGROUND OF THE INVENTION

1. Field of Invention

This invention relates to regulation of plant osmoregulation and transpiration through guard cells. In particular, the present invention relates to the regulation of guard cell opening through the activity of the AtCHX20 promoter. The AtCHX20 promoter serves as a powerful tool to manipulate the opening and closing of guard cells and thus the ability to control water loss and gas exchange of plants.

Although all cells in an organism contain the same genetic make up, each cell expresses a particular subset of genes that give the cell its particular structure and function. Each protein-coding gene is under the control of its own promoter which consists of a distinct DNA sequence. In plants, the 'promoter' or regulatory region (usually 1-3 kb in length) is located immediately upstream of the structural gene. Here evidence is provided showing that AtCHX20 is specifically and highly expressed in guard cells. These results demonstrate that AtCHX20 gene is expressed under the control of a guard-cell specific promoter. If so, the guard cell-specific promoter region of AtCHX20 can be used to regulate expression of any gene in guard cells. The promoter region will be a powerful tool when it is used to express genes and proteins that significantly affect the opening and closing of stomatal pores.

2. Description of Prior Art

Most land plants have the ability to regulate gas exchange and transpiration by the opening and closing of the stomatal aperture. The movement of a pair of special epidermal cells or guard cells, controls the size of the stomatal aperture and so regulates the extent of water loss via transpiration and also regulates $CO_2$ uptake into the leaf for photosynthetic carbon fixation.

At the beginning of the day, light stimulates the opening of the stomatal aperture of most plants by increasing solute concentration and decreasing water potential, thus attracting water into the guard cells (for review, see Assmann, 1993; Schroeder et al., 2001; Roelfsema and Hedrich, 2005). The concomitant increase in turgor pressure causes the guard cells to swell and pushes the pair of cells apart, increasing the aperture between the two cells.

At dusk, the aperture size decreases and becomes nearly closed at night, thus reducing transpiration and gas exchange. During drought, the amount of abscisic acid (ABA) reaching the guard cells can increase, triggering the efflux of ions and loss of water and turgor pressure, leading to closure of the stomatal aperture. ABA can also prevent light-induced stomatal opening (Schroeder et al., 2001).

Studies of the osmotic changes driving guard cell movement have focused mainly on the roles of plasma membrane (PM)-associated transporters and signaling elements regulating the transporters (Blatt, 2000; Fan et al., 2004; Roelfsema and Hedrich, 2005). Advances in understanding their activity have been triggered by the ability to patch guard cell PM, to study transport across this membrane, and to analyze mutants.

It has been found that light-induced stomatal opening starts when light activates the PM $H^+$-ATPase causing membrane hyperpolarization. $K^+$ then enters via inward-rectifying channels, and anions enter via predicted $H^+/Cl^-$ and $H^+/NO_3^-$ symporters. Ion, malate, and sugar accumulation decreases the water potential; thus, water is taken up, increasing turgor pressure.

More recently, several inward-rectifying $K^+$ channels (e.g. KAT1, KAT2, AKT1) in stomatal opening have been identified at the molecular level (for review, see Very and Sentenac, 2003; Fan et al., 2004). Nitrate is one counterion that balances $K^+$ uptake via an $H^+$-coupled $NO_3^-$ symporter (AtNRT1.1; Guo et al., 2003). Stomatal closing begins when the membrane depolarizes, causing the opening of outward-rectifying $K^+$ channels. Dark-induced depolarization is caused by deactivation of the PM $H^+$ extrusion pump and by opening of anion efflux channels. Loss of $K^+$ and anions leads to a decrease in solute concentration, water efflux, and loss of guard cell turgor. GORK is suggested to be the major outward-rectifying $K^+$ channel (Hosy et al., 2003); however, the molecular identity of PM R-type and S-type anion channels is still unclear. Genetic evidence suggests that the AtMRP5 ABC (ATP-binding cassette) transporter mediates anion efflux (Klein et al., 2003).

Less well understood are the changes of intracellular compartments during guard cell movement. As guard cells increase in volume, the size of vacuoles increases considerably (Louget et al., 1990), indicating that the bulk of solutes entering guard cells accumulate in the large vacuoles (MacRobbie, 1999), which is iso-osmotic with the cytosol. When stomata close, guard cells are filled with numerous relatively small vacuoles. Many vacuolar transporters identified in plant cells are expressed in guard cells according to the Affymetrix 8K GeneChip® results (Leonhardt et al., 2004). Endomembrane compartments, including vacuoles, are acidified by electrogenic $H^+$-pumping vacuolar-type ATPases (V-ATPase) and $H^+$-pumping pyrophosphatases (Sze, 1985; Rea and Poole, 1993). Thus, it is very likely that the vacuolar membrane potential (DCvac) slightly positive inside the lumen relative to the cytosolic side and DpH acidic inside the lumen relative to the cytosol could drive the accumulation of $K^+$ into the lumen via $H^+$/cation antiporters.

Anions, including $Cl^-$ and $NO_3^-$, were predicted to enter vacuoles via anion-specific channels because these anions rapidly dissipate the membrane potential generated by the V-ATPase of intracellular vesicles (Sze, 1985), although recent evidence showed that $NO_3^-$ enters vacuoles through a $H^+$-coupled $NO_3^-$ antiporter (ClC-a) at the vacuolar membrane (De Angeli et al., 2006).

VK channel activity previously characterized to function in $K^+$ release from vacuoles in response to elevated cytosolic $Ca^{2+}$ (Ward and Schroeder, 1994) is mediated by TPK+/KCO1 (Bihler et al., 2005). FV channels are inhibited by elevated cytosolic $Ca^{2+}$ and may modulate $K^+$ uptake into vacuoles during stomatal opening (Pei et al., 1999).

Until the disclosure of the present invention, it was not known whether there was a promoter that regulated gene expression in guard cells with high specificity. The applicants herein have identified a promoter which can be used to regulate the opening and closing of these guard cells.

SUMMARY OF THE INVENTION

In accordance with the present invention, the inventors now provide genetic evidence for the role of a novel endomembrane transporter in guard cell movement. In particular, the inventors have found that *Arabidopsis* (*Arabidopsis thaliana*) AtCHX20 protein belongs to a large family of 28 cation/proton exchangers whose functions until now, have been largely unknown (Sze et al., 2004).

The guard cell specific promoter of the AtCHX20 gene (or At3g53720) was identified and demonstrated in the model plant *Arabidopsis thaliana* (Padmanaban et al. Plant Physiol. 2007 in press). The inventors have now shown that the guard cell specific promoter can serve as a powerful tool to manipulate the opening and closing of guard cells and thus the ability to control water loss and gas exchange of plants. Such a tool can be particularly useful when applied to crops and other plants of economic importance, thus the present inventors have identified homologous genes in other plants, which fall within the scope of this invention.

The inventors herein disclose a new promoter of a transporter gene that participates in guard cell movement. Nearly nothing is known about the roles of cation/proton antiporter (CPA) genes in guard cells, although several members of the superfamily, including NHX1, are expressed there. The AtCHX family was uncovered recently as a novel subfamily (Maser et al., 2001; Sze et al., 2004), although the biochemical properties of this family remained uncharacterized until recently (Maresova and Sychrova, 2006). Previous studies showed 18 CHXs are preferentially expressed in pollen and six AtCHXs are highly expressed in roots and/or shoots (Cellier et al., 2004; Sze et al., 2004; Hall et al., 2006). The inventors have now found that AtCHX20 is preferentially expressed in guard cells using microarray and promoter-driven GUS reporter activity analyses.

The inventors found that AtCHX20 consistently caused mutant KTA40-2 (Δena1-4 Δnha1 Δnhx1 Δkha1) to be more sensitive to salt. In another salt-sensitive yeast mutant, AXT3 (Δena1-4 Δnha1 Δnhx1), expression of AtCHX20 also resulted in increased sensitivity to moderate NaI stress and high K$^+$, although AtNHX1 or AtNHX2 conferred moderate tolerance to Na$^+$ stress (data not shown) as shown before (Yokoi et al., 2002). Furthermore, AtCHX20 was unable to confer hygromycin B tolerance. Thus, AtCHX20 is functionally distinct from the vacuolar AtNHX1 that sequesters excess Na$^+$ or K$^+$ into vacuoles and confers tolerance to high Na$^+$ or K$^+$ and to hygromycin B (Pardo et al., 2006).

In addition, AtCHX20 function appears to be important particularly when K$^+$ is depleted and when the external pH is slightly alkaline. This is shown by improved growth of KTA40-2 expressing AtCHX20 at pH 7.5 and when $[K^+]_{ext}$ was low (between 0.4 and 3 mM).

The present invention shows the following characteristics of AtCHX20, which are: (1) AtCHX20 is mainly localized to endomembranes, possibly endosomes, in plant cells; (2) phylogenetic analysis showed that AtCHX20 is a cation/proton antiporter belonging to the CPA2 subfamily (Sze et al., 2004); and (3) AtCHX20, like ScKHA1, enhanced yeast growth at basic pH when K$^+$ ext concentration was low (Maresova and Sychrova, 2005).

The findings of the present invention also indicate that, in addition to a vacuolar H$^+$-pump, AtCHX20 has a role in sustaining growth at pH 7.5 when other K+ (Na$^+$)/H$^+$ antiporters are absent. Thus, AtCHX20 fills a role in pH regulation in plants.

It has also been found that CHX helps distribute cellular K$^+$ when the external pH is alkaline. It is well known that when medium K$^+$ is low or nearly depleted (0.1 mM), energy-dependent K$^+$ uptake is needed to maintain $[K^+]_{cyt}$ at millimolar levels (Rodriguez-Navarro, 2000). However, when the medium pH is slightly alkaline, the proton-motive force for K$^+$/H$^+$ symport at the PM is reduced and the alkalinization of the cytosol could inactivate the PM H$^+$ pump. To counter the reduced proton-motive force at the PM, acidification of intracellular compartments by yeast VMA could energize accumulation of K$^+$ from the cytosol into internal compartments using a K$^+$/H$^+$ antiporter. Due to the small volume of vesicles and internal compartments of the endomembrane system, a proton electrochemical gradient (acidic in the lumen) forms rapidly energizing K$^+$ accumulation. Accumulated K$^+$ can then be redistributed to the cytosol and other compartments by release via cation channels and by vesicle trafficking. Our results and model are consistent with genetic studies of a related protein, CHX17, where K$^+$ starvation induced an increase of CHX17 transcripts in wild-type plants; and K$^+$ starvation caused a 20% decrease in K$^+$ content of chx17 mutant roots (Cellier et al., 2004).

It is an object of the present invention to demonstrate functional expression of AtCHX20 in a salt-sensitive yeast (*Saccharomyces cerevisiae*) strain providing evidence that AtCHX20 has a role in pH regulation and K$^+$ transport.

It is also an object of the present invention to show that AtCHX20 is preferentially expressed in guard cells of plants.

These and other objects of the invention, as well as many of the attendant advantages thereof, will become more readily apparent when reference is made to the following detailed description of the preferred embodiments.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIG. 3A shows that AtCHX20 did not confer tolerance to hygromycin. Five microliters of yeast were spotted on YNB medium at pH5.5, with or without hygromycin B (150 mg/mL), and incubated for 4 d. FIG. 3B shows that AtCHX20 fused to GFP conferred tolerance to the KTA40-2 strain at basic pH. Yeast was spotted on medium adjusted to pH 7.5 with Arg base and incubated for 2 d.

FIG. 4A illustrates expression of the CHX gene family on the ATH1 whole genome GeneChip®. Microarray analysis was performed with RNA extracted from purified guard cells and from mesophyll cells of wild-type plants. Bar graph shows normalized expression levels of CHX genes present on the chip in guard cells (GC; light bars) and in mesophyll cells (MC; dark bars). Relative expression of KAT1, a guard cell-expressed gene, serves as a positive control. FIG. 4B, depicts AtCHX20 promoter activity. PromoterTGUS activity in cotyledon (a), sepals of young flowers (b), anther (c), rosette leaf (d), a magnified leaf (e), and root cap (f) is shown. GUS activity was seen after 2 h in 1.0 mM X-Gluc. Scale bars=200 mm (a and b), 100 mm (c, d, and f), and 10 mm (e).

FIGS. 8A-B illustrate ABA-induced stomatal closure. Isolated epidermal cells from wild type or chx20-3 were incubated in opening solution for 3 h under light. Then ABA was added to 1.0 mM and stomatal pore and guard cell length was measured at 30-min intervals. 8A, ABA reduces aperture size. Size is expressed as a ratio of maximal aperture size per length of guard cells. 8B, Percentage of closure. The relative percentage of closure is estimated using the light-induced aperture at zero time as 100%. Data are from two independent experiments. Bar=SE.

FIG. 9 shows the deduced AtCHX20 protein sequence (SEQ ID NO: 11) compared with yeast KHA1 (SEQ ID NO: 12). The transmembrane domains show high similarity to yeast ScKHA1 (Acc. No P40309). Identical, very similar and similar residues between the two proteins are designated as *, : and., respectively. The TM regions indicated by shading and black lines were determined by TMHMM2 program in SMART.

FIG. 10 discloses a table showing gene sequences in other plants that encode proteins with high homology to AtCHX20 and most likely serve the same function within those plants. The plants include rice, *Medicago*, poplar and corn. The promoter regions and lengths of genes homologous to AtCHX20 are identified on BAC clones whenever available.

DETAILED DESCRIPTION AND PREFERRED EMBODIMENTS

Figure 1A:
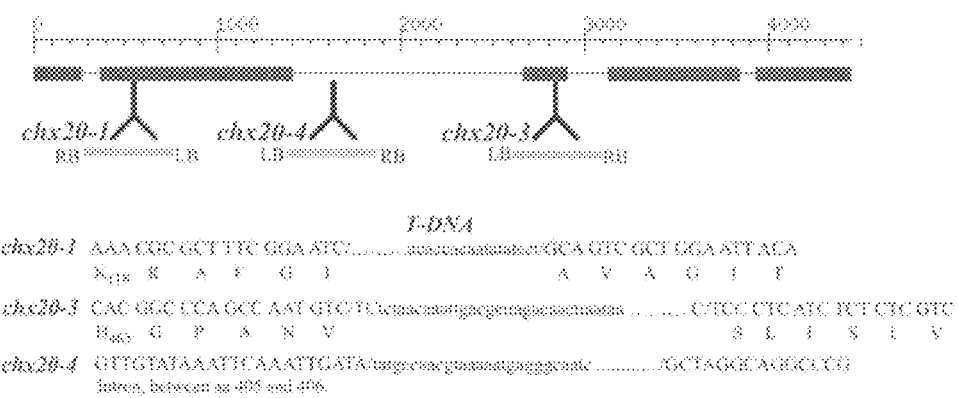
FIGS. 1A and 1B illustrate the AtCHX20 gene organization and protein sequence. 1A shows the genomic structure of AtCHX20 that was confirmed by the cDNA sequence (corresponding to accession no. AY926476, BT002529 (cDNA), and F5K20_20 (genomic DNA). The positions of three independent T-DNA insertional mutants are shown. The T-DNA sequences are shown in lowercase. Mutants chx20-1 (SEQ ID NOS 1-4, respectively, in order or appearance) and chx20-3 (SEQ ID NOS 5-8, respectively, in order or appearance) correspond to SALK lines SALK_031420 and SALK_011726, and chx20-4 (SEQ ID NOS 9-10, respectively, in order or appearance) was obtained from Genoplante. 1B shows the predicted topology of AtCHX20 in the membrane of the cell.

All experiments were conducted with *Arabidopsis* (*Arabidopsis thaliana*) ecotype Col-0. Wild-type, mutant, and transgenic plants were grown under the same conditions.

Plants were grown in Miracle-Gro® potting soil (Scotts). Seeds in soil were stratified at 4° C. for 3 d and then plants were grown in controlled environment chambers at 20° C. under illumination of 150 µE $m^{-2}$ $s^{-1}$ with a 16-h photoperiod. Two weeks after germination, plants were given Miracle-Gro® plant food at 20-d intervals. To test for promoter TGUS expression, transgenic seeds were grown under light (150 mE m22 s21) at 20° C. on plates containing 0.53 Murashige and Skoog (1962) salts and 1.0% agar, pH 5.8.

Transformation of Plants

The present invention also includes vectors containing the nucleic acids of the invention. Suitable vectors according to the present invention comprise a gene encoding a ketolase enzyme as described above, wherein the gene is operably linked to a suitable promoter. Suitable promoters for the vector can be constructed using techniques well known in the art (see, for example, Sambrook et al., Molecular Cloning: A Laboratory Manual, Cold Spring Harbor Laboratory, Cold Spring Harbor, N.Y., 1989; Ausubel et al., Current Protocols in Molecular Biology, Greene Publishing and Wiley Interscience, New York, 1991). Suitable vectors for eukaryotic expression in plants are described in Fray et al., (1995; Plant J. 8:693-701) and Misawa et al., (1994; Plant J. 6:481-489). The vectors of the present invention can additionally contain regulatory elements such as promoters, repressors, selectable markers such as antibiotic resistance genes, etc., the construction of which is very well known in the art.

The term "derivative" means, within the context of the present invention, that the sequences of these molecules differ from the sequences of the nucleic acid molecules according to the invention or to be suitably employed in accordance with the invention in one or more positions and exhibit a high degree of homology to these sequences. Homology in the present context means a sequence identity of at least 60%, preferably over 70%, and especially preferably over 85%, in particular over 90% and very especially preferably over 95%. The deviations relative to the nucleic acid molecules according to the invention or to the nucleic acid molecules to be suitably employed in accordance with the invention may have originated by means of one or more deletions, substitutions, insertions (addition) or recombinations.

Furthermore, homology means that a functional and/or structural equivalence exits between the nucleic acid molecules in question and the proteins encoded by them. The nucleic acid molecules which are homologous to the molecules according to the invention or to the molecules to be suitably employed in accordance with the invention and which constitute derivatives of these molecules are, as a rule, variations of these molecules which constitute modifications which exert the same, a virtually identical or a similar biological function. They may be naturally occurring variations, for example sequences from other plant species, or mutations, it being possible for these mutations to have occurred naturally or to have been introduced by directed or random mutagenesis. The variations may further be synthetic sequences. The allelic variants may be naturally occurring variants or else synthetic variants or variants generated by recombinant DNA technology.

The pDCHX20-GFP fusion constructs were transiently expressed in onion epidermal cell or in *Arabidopsis* mesophyll protoplast (Kovtun et al., 2000). Constructs were introduced into onion cells using biolistic gun. Tungsten particles were coated with plasmid DNA (Bio-Rad Laboratories, Hercules, Calif.) and the mixture was loaded onto plastic filter SWINNEX® (Millipore, Billerica, Mass.) then dried on room temperature. The coated filter was assembled into the particle inflow gun and bombarded into onion leaf using a 50-ms pulse of helium (50 lb/in2). Bombarded tissues were incubated for 12 to 16 h at room temperature and epidermal peel was analyzed.

To express GFP-tagged protein in *Arabidopsis*, mesophyll protoplasts, were prepared first. Rosette leaves of 3 to 4 week old plants grown at 20° C. under 14 h photoperiod were harvested. The epidermal layer was removed and the mesophyll cells were directly incubated with the enzyme solution containing 11 cellulase R10, 0.2-0.4% macerozyme R10, 0.4 M mannitol, 20 mM KCl, 20 mM MES, pH 5.7, 10 mM $CaCl_2$, 5 mM β-mercaptoethanol and 0.1% BSA in the dark for 2.5 h at 22° C. Protoplasts were separated from undigested material by filtration through a 140 μm nylon mesh, and collected by centrifugation at 100×g in a round-bottomed tube for 2 min. The protoplast pellet was washed in W5 solution consisting of 154 mM NaCl, 125 mM $CaCl_2$, 5 mM KCl and 2 mM MES pH 5.7). For transfection, 10 μg plasmid DNA (pDCHX20-GFP or other GFP-tagged markers, see Table II) were added to 100 μl protoplast ($2 \times 10^4$ protoplast). After gentle mixing, 110 μl PEG solution consisting of 400 mM mannitol, 100 mM $CaCl_2$, 40% PEG 4000 was added and mixed carefully. Following incubation at room temperature for 30 min, the transfection mixture was carefully diluted with W5 solution and spun at 100×g, and then the protoplasts were suspended in 100 μl W5 solution and incubated at room temperature for 12-16 h in the dark.

ATH1 GeneChip® Analysis

The whole genome ATH1 GeneChip® (Affymetrix, Inc., Santa Clara, Calif.) experiments were performed with guard cell and mesophyll cell RNA that was extracted from WT *arabidopsis* plants using methods described before with the 8k GeneChip® (Leonhardt et al., 2004). Briefly, guard cell and mesophyll cell protoplasts were purified from rosette leaves of ~100 *Arabidopsis* plants. Guard cells and mesophyll cells were collected simultaneously, and RNA was extracted, thus resulting in equal durations from leaf excision to RNA extractions for guard cells and mesophyll cells. Transcription inhibitors, actinomycin D (33 mg/L) and cordycepin (100 mg/L), were added to inhibit gene expression during protoplast isolation. Total RNA from guard cell protoplasts and from mesophyll protoplast were extracted and 10 μg total RNA of each was used for ATH1 whole genome chip hybridization. Overall intensity normalization for the entire probe sets was performed using Affymetrix Microarray Suite 5.0®. Using the GeneChip® Suite 5.0 default parameters, the detection P-value and the signal value were calculated for each probe set from each independent guard cell and mesophyll cell hybridization.

The AtCHX20 promoter was transcriptionally fused to the GUS gene. A 2-kb region upstream of AtCHX20 was amplified by PCR. Primers CHX20-PF and CHX20-PR have SalI and BamHI restriction sites, respectively.

TABLE I

Primers used in this study.

| Purpose | Primer | Primer sequence |
|---|---|---|
| Promoter::Gus | CHX20-PF | 5'-CGCGTCGACACTCTCTACCTAGAACA GTTCGCTGTAC3' (SEQ ID NO: 14) |
| | CHX20-PR | 5'-CGCGGATCCTTTGGGGATTTCAAAGG ACTCTCTTAT-3' (SEQ ID NO: 15) |
| cDNA | X20Cf | 5'-GGGGACAAGTTTGTACAAAAAAGCAG GCTCGTCGATAAGAGAGTCCTTTGAA A-3' (SEQ ID NO: 16) |
| | X20Cr | 5'-GGGGACCACTTTGTACAAGAAAGCTG GGTCTCCGTTAATACTTAGAGAAGACT C-3' (SEQ ID NO: 17) |
| CHX20 Sequence | S1 | 5'-GTGATCCGTAACACTCTCTA-3' (SEQ ID NO: 18) |
| | S2 | 5'-GTCAGCGATTGATTGAACGA-3' (SEQ ID NO: 19) |
| | S3 | 5'-GTCCATCCGAACCACCAAGA-3' (SEQ ID NO: 20) |
| Mutant | LBA1 | 5'-TGGTTCACGTAGTGGGCCATCG-3' (SEQ ID NO: 21) |
| salk031420 chx20-1 | chx20-1-LP | 5'-GACACTAACGGACTCTTTTTCTCTCC AC-3' (SEQ ID NO: 22) |
| | chx20-1-RP | 5'-GAGAGTCCTTTGAAATCCCCAAAATG CC-3' (SEQ ID NO: 23) |

TABLE I-continued

Primers used in this study.

| Purpose | Primer | Primer sequence |
|---|---|---|
| salk011726 chx20-3 | chx20-3-LP | 5'-ATAGTTCTTCTCCTTGCCTTTAGACGGTG-3' (SEQ ID NO: 24) |
| | chx20-3-RP | 5'-TGTTTACGTAATCGTCACTTACTGATCCA-3' (SEQ ID NO: 25) |
| CHX20-4F | chx20-4F-P1 | 5'-ACTATACCGAAAGATGGAGAGTTTG-3' |

TABLE I-continued

Primers used in this study.

| Purpose | Primer | Primer sequence |
|---|---|---|
| | | (SEQ ID NO: 26) |
| | chx20-4F-P2 | 5'-AAATTGCAACCGTGTCCATCAGTC-3' (SEQ ID NO: 27) |
| RT-PCR CHX20 | X20TRT-F1 | 5'-TTTGAAATCCCCAAAATGCCCTTCAACATAACCTCCGTGAAAACCTCATC-3' (SEQ ID NO: 28) |
| | X20TRT-R1 | 5'-CTTTTTCTCCTTGCCTATGTTGAGTACAATGAGCTCCACTAAACCTTTA-3' (SEQ ID NO: 29) |
| | X20TRT-F2 | 5'-TAAAGGTTTAGTGGAGCTCATTGTACTCAACATAGGCAAGGAGAAAAAG-3' (SEQ ID NO: 30) |
| | X20TRT-R2 | 5'-CCATGCATTAAGCCGAAGTTTAAGTACTAGATCAATTTATTTATTGT-3' (SEQ ID NO: 31) |
| | X20TRT-F3 | 5'-TCTCTCTCGTCGAGTCCATCCGAACCACCAAGATAC-3' (SEQ ID NO: 32) |
| Actin 11 | Act-S (sense) | 5'-ATGGCAGATGGTGAAGACATTCAG-3' (SEQ ID NO: 33) |
| | Act-AS (anti) | 5'-GAAGCACTTCCTGTGGACTATTGA-3' (SEQ ID NO: 34) |

The amplified products were digested and fused with GUS in pRITA I plasmid. Clones were confirmed by sequencing. The region containing the CHX20 promoter and GUS was subcloned into the binary vector pMLBart using NotI and named CHX20TGUS (Table II).

All ATCHX20 constructs were generated in this study. Kan, Spec, and Amp refer to kanamycin-, spectinomycin- and ampicillin-resistance indicators. Vectors for expression of GFP-tagged markers, TAP-GFP(S65T)-CPK9 and TAP-GFP(S65T)-TIP were obtained from JY Lee (Univ. Delaware) and JF Harper (Univ. Nevada). P35S::spGFP-HDEL (Hawes et al. 2001) was obtained from Nina Federoff (Penn State Univ), and ST-GFP and ST-RFP (Lee et al. 2002) were gifts of Inhwan Hwang (Pohang Univ.). Ara6-GFP was provided by T. Ueda (Ueda et al. 2001).

TABLE II (HDEL disclosed as SEQ ID NO: 13)

| Construct name | Vector | Gene insert | E. coli Marker | Host | Selection Marker | Promoter |
|---|---|---|---|---|---|---|
| pECHX20 | pDONR221 | CHX20 | Kan | — | — | — |
| pDES-c1 | pYES-DEST52 | — | Amp | yeast | URA3 | GAL1 |
| pDYES-CHX20 | pYES-DEST52 | CHX20 | Amp | yeast | URA3 | GAL1 |
| pDCHX20-GFP | pK7FWG2 | CHX20 | Spec | plant | Kan | CAMV35S |
| CHX20::GUS | pMLBart | CHX20 | Spec | plant | BASTA | CHX20 |
| GFP | pMLBart | eGFP | Spec | plant | BASTA | CaMV35S |
| TAP-GFP(S65T)-CPK9 | pdGC | CPK9 | Amp | plant | | CAMV35S |
| TAP-GFP(S65T)-TIP | pdGC | TIP | Amp | plant | | CAMV35S |
| P35S::spGFP-HDEL | pBSK | | Amp | plant | | CAMV35S |
| ST-GFP | pBSK | ST | Amp | plant | | CAMV35S |
| pDRCHX20 | pYESDR196 | CHX20 | Amp | yeast | URA3 | PMA1 |
| pGWFDRCHX20 | pGWFDR196 | CHX20 | Amp | yeast | URA3 | PMA1 |
| p2GWFCHX20 | p2GWF7 | CHX20 | Amp | plant | | CAMV35S |
| Ara6-GFP | pHTS13 | Ara6 | Amp | plant | | CAMV35S |

To isolate CHX20 cDNA, total RNA was isolated from leaves of wild-type *Arabidopsis* and first-strand cDNA was synthesized using reverse transcriptase. Primers X20Cf and X20Cr were used to amplify the cDNA by 25 cycles (94° C. 30 s, 55° C. 30 s, and 72° C. 90 s). The forward and reverse primers contain attB1 and attB2 sequences for Gateway recombination cloning. Gel-purified PCR products were recombined with pDONR221 using BP Clonase according to the manufacturer's method (Invitrogen). Resulting clones were sequenced using forward and reverse M13, S1, S2, and S3 primers. The correctly spliced clone with the longest ORF was named entry clone pECHX20.

To make a CHX20-GFP fusion construct, the AtCHX20 coding sequence from pECHX20 was recombined to the binary vector pK7FWG2 (Karimi et al., 2002) using LR Clonase to give an in-frame fusion of enhanced GFP at the C tail of CHX20 or pDCHX20-GFP. For expression in yeast (*Saccharomyces cerevisiae*), AtCHX20 from pECHX20 was recombined into a yeast-*Escherichia coli* shuttle vector, pYES-DEST52, to yield PDYES-CHX20.

The binary vectors with AtCHX20 promoter::GUS or pDCHX20-GFP were introduced stably into *Arabidopsis* using *Agrobacterium tumefaciens*-mediated floral dip (Clough and Bent, 1998). Transformants were selected on 0.53 Murashige and Skoog plates containing kanamycin (50 mgmL21) or on soil by spraying with BASTA. T2 plants were analyzed for GUS expression or CHX20-GFP fluorescence. pDCHX20-GFP or other GFP-tagged constructs (Table II) were transiently expressed in onion (*Allium cepa*) epidermal cell or in *Arabidopsis* mesophyll protoplasts (Kovtun et al., 2000) and observed after 12 to 16 h.

GFP Microscopy

The cells or tissues from transient and stable transformants were imaged for GFP fluorescence using a Zeiss LSM 510 laser-scanning confocal microscope with a 103 dry 0.8 numerical aperture lens and a 633 1.2 numerical aperture water immersion lens (Zeiss). The filter settings are Ex 488 nm/Em BP 510 to 530 nm for GFP, and Ex 488 nm/Em LP 570 nm for chlorophyll. Sometimes optical sections of approximately 5-mm increments were made to visualize the signal patterns at the medial to the peripheral plane. Images were assembled in Photoshop (Adobe Systems Inc., CA).

GUS Staining

At least six independent transgenic lines were tested for GUS activity. Tissues were incubated in a mixture containing 84 mM sodium phosphate, pH 7.0, 0.5 mM potassium ferrocyanide, 0.5 mM potassium ferricyanide, 0.5% Triton X-100, and 1.5 mM 5-bromo-4-chloro-3-indolyl-b-D-GlcUA (X-Gluc) at 37° C. for 2 h. Samples were then fixed in 70% ethanol overnight to clear chlorophyll. Photographs were taken under a Nikon® stereoscopic zoom microscope SMZ1000 or with differential interference contrast using a Nikon® E600 microscope.

ATH1 GeneChip® Analysis

The ATH1 23K GeneChip® experiment was performed with guard cell and mesophyll cell RNA extracted from wild-type plants using methods described for the 8K chip (Leonhardt et al., 2004). Overall intensity normalization for the entire probe set was performed using Affymetrix Microarray Suite 5.0. Using the GeneChip® Suite 5.0 default parameters, the detection P value and the signal value were calculated for each probe set from each independent guard cell and mesophyll cell hybridization.

Yeast strains used in the study are (1) AXT3 (MATα his 3-11 leu2-112 trp1-1 ade2-1 ura3-1 ena1Δ::his3::ena4Δ:: nha1Δ::leu2 nhx1Δ::trp1 in W303-1B); (2) KTA40-2 (MATα ade2-1 can1-100 his3-11,15 leu2-3,112 trp1-1 ura3-1 mall0 ena1Δ::his3::ena4Δ nha1Δ::lew2 nhx1Δ::trp1 kha1Δ:: kanMX); and (3) LMB 01 (MATα ade2-1 can1-100 his3-11, 15 leu2-3,112 trp1-1 ura3-1 mall0 ena1Δ::his3::ena4Δ nha1Δ::leu2 kha1Δ::kanMX) (Quintero et al., 2000; Maresova and Sychrova, 2005). Yeast was transformed with plasmid DNA using the lithium acetate method (Gietz et al., 1992) and the resulting transformants were selected on SC medium minus Ura (0.67% YNB, 2% Glc, 2% drop-out mix, 2% agar).

Fresh cells grown in liquid medium were washed and suspended in water and then adjusted to OD600 of 1.0 (13). Ten-fold serial dilutions of the cells were prepared with sterile water and 5 mL of each dilution was spotted on plates containing appropriate SC minus Ura (0.67% YNB, 2% Glc or Gal, 2% drop-out mix minus Ura, 2% agar) or SDAP minus Ura and adjusted to the desired pH. To reduce $K^+$ and $NH_4^+$, modified SDAP medium was used. SDAP minus Ura medium consisted of 10 mM Arg-HCl (or Arg base), 2% (w/v) Glc or Gal, 2% drop-out mix minus Ura, 2 mM MgSO4, 0.9 mM CaCl2, trace minerals, vitamins, and 2% agar. Medium containing Arg-HCl was adjusted to pH 4.5 with tartaric acid and to pH 5.5 to 6.0 with 10 mM HEPES and Tris. For pH 7.0 to 7.5, medium contained Arg base and 10 mM HEPES and was adjusted to desired pH with tartaric acid or Tris. Plates were incubated at 30° C. for 2 d and the relative growth of yeast was recorded using a Nikon Coolpix 995 digital camera.

For some experiments, 3-d yeast cells were cultured in liquid YNB medium containing 0.67% YNB without amino acids, 2% Glc, 0.01% adenine, 0.01% Trp, and 10 mM MES adjusted to pH 5.5 with Arg base and grown for 18 h at 30° C. One-milliliter cultures were diluted to 6 ml with YNB medium without Glc and then starved for 18 h at 30° C. Starved cells were washed with 6 mL water, pelleted, and suspended in water. Cell density was normalized to OD 600 of 0.2 and subjected to 10-fold serial dilution. Five-microliter aliquots were spotted on modified YNB plates at pH 7.5 or 5.5. The YNB medium also contained 2% agar, 0.02% bromocresol purple (catalog no. 860891; Sigma), and 20 mM MES adjusted to either pH 5.5 or 7.5 with Arg base. Hygromycin B, when added, was 150 mg/mL (catalog no. H7772; Sigma Co., St. Louis, Mo.). Plates were incubated at 30° C. for 2 to 4 d.

T-DNA insertional mutants of chx20 (Alonso et al., 2003) were detected in the SALK database. Homozygous mutants, SALK 031420 (chx20-1), and SALK 011726 (chx20-3) seeds were first identified by PCR using LBa1 primer and CHX20-specific primers: CHX20-1-LP, CHX20-1-RP, CHX20-3-LP, CHX20-3-RP, CHX20-4F-P1, and CHX20-4F-P2 (Supplemental Table S1). The site of insertion was verified by sequencing.

To detect AtCHX20 transcript, total RNA isolated from chx20-1, chx20-3, and chx20-4 mutant and wild-type plants was reverse transcribed. Primer sets (Table I) F1 (from 215 to 30 bp) and R1 (1,300-1,252 bp); F2 (1,252-1,300 bp) and reverse primer R2 (3#-untranslated region); and F3 (1,506-1, 541 bp) and R2 are expected to amplify products of 1,230, 1,413, and 1,158 bp in wild-type plants, respectively.

To test light-induced stomatal opening (Kwak et al., 2001), leaves were excised from 3-week-old wild-type and chx20 mutants. Leaves were separated into two batches and placed in aluminum foil-covered containers in the opening solution (5 mM KCl and 10 mM MES-KOH at pH 6.15) for 3 h. The dark-adapted leaves were then exposed to white light (approximately 150 mE $m^2$ $s^{-1}$) or dark for 3 h at 20° C. Leaves were blended and filtered through 200-mm nylon mesh. Isolated epidermis was observed under a microscope (Axiovert, 40 CFL; Zeiss), and 20 stomata were measured for each condition.

To study the effect of KCl concentration, isolated epidermal cells from wild type or chx20-3 were incubated in 10 mM MES-Tris at pH 6.15 without $K^+$ for 3 h in the dark and then KCl was added to a final concentration of 0.1, 1, and 10 mM before exposure to 3 h of light. To test pH, the pH 6.15 medium was buffered with 10 mM MES-Tris and that of pH 7.0 to 8.0 was adjusted with 10 mM HEPES-Tris. To test ABA-induced stomatal closure, isolated epidermal cells from wild type or chx20-3 were incubated in opening solution with light for 3 h, then ABA was added to 1 mM and stomatal pore size and guard cell length were measured at 30-min intervals using Scion image analysis. The stomatal aperture was measured as the maximal width between the inner cuticular lips.

EXAMPLE 1

AtCHX20 cDNA Isolation and Predicted Protein

To characterize the AtCHX20 protein, Applicants first extracted total RNA from *Arabidopsis thaliana* to identify the cDNA for AtCHX20. To obtain AtCHX20 (At3g53720) cDNA, total RNA was extracted from rosette leaves of 3-week-old *Arabidopsis* plants and first-strand cDNA was used to amplify the coding sequence. The primers at the start and end of the open reading frame (ORF; X20Cf and X20Cr; Table I) were designed based on the genomic sequence. A 2.5-kb fragment was amplified and its sequence (AY926476; SEQ ID NO:37) matched the coding sequence that is formed from five exons (FIG. 1A).

Figure 1B:
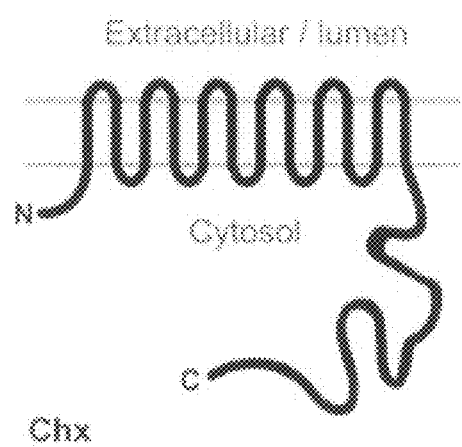

The predicted AtCHX20 protein of 842 residues (SEQ ID NO: 36) has two domains: (1) a hydrophobic domain (434 residues) with 10 to 12 transmembrane spans at the amino half; and (2) a large hydrophilic domain of 403 residues at the carboxylic end (FIG. 1B). The hydrophobic domain shows extensive similarity (56.5% similarity, 33.6% identity; E value of 1e-54) to the transmembrane domain of yeast ScKHA1 protein, although the long carboxylic tail of the two proteins did not align (10.6% identity; no E value; Table I). These results suggested that the transport activities of AtCHX20 and yeast ScKHA1 are similar.

EXAMPLE 2

Identification of Function of AtCHX20 in Yeast

The coding sequence of AtCHX20 was cloned in pYES-DEST52 yeast expression vector under the Gal promoter. Yeast mutants with disrupted kha1 gene alone exhibited no obvious phenotype (Maresova and Sychrova, 2005), so we expressed AtCHX20 in a yeast mutant (KTA40-2). This strain lacks functional vacuolar and PM-localized $Na^+/H^+$ antiporters, PM $Na^+$ pumps (Dnhx1 Dnha1 and Dena1-4), as well as the putative $K^+/H^+$ exchanger (Dkha1; Maresova and Sychrova, 2005). Strain KTA40-2 is highly sensitive to salt and to high $K^+$, so the transformant (KTA40-2-CHX20) was tested for its ability to grow on moderate levels of $Na^+$ and very high $K^+$.

Figure 2A:
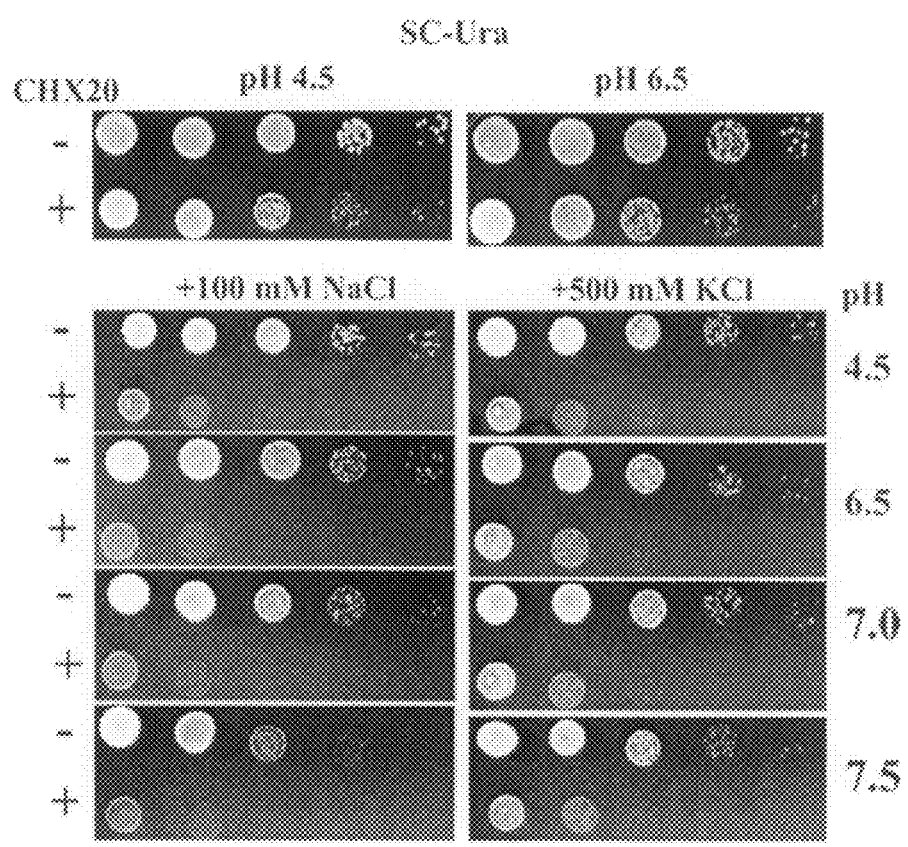
FIGS. 2A, 2B and 2C show a yeast mutant KTA40-2 expressing AtCHX20 is tolerant to low K$^+$ at alkaline pH. 2A illustrates the mutant sensitivity to moderate NaCl stress and high KCl. AtCHX20 (1) or vector only (2) was expressed in a KTA40-2 mutant. Growth was tested on standard SC medium (containing 8 mM K$^+$, 1.7 mM Na$^+$) or medium supplemented with 100 mM NaCl or 500 mM KCl at pH 4.5 to 7.5. Cells were normalized to 1.0 A600 and then serially diluted by 10-fold. Five microliters of each dilution was spotted. 2B discloses the yeast tolerance to low K$^+$ at pH 7.5. Yeast mutant KTA40-2 was transformed with either vector pYES-cl alone or with pDYES-CHX20, and the culture was serially diluted and plated on SDAP-Ura at pH 4.5 to 7.5 with no added $K^+$ as described above. 2C shows the $K^+$ concentration dependence of the yeast. KTA40-2 was serially diluted and plated on medium at pH 7.5 supplemented with 0, 1, 3, 25, and 50 mM KCl.

Surprisingly, mutant yeast expressing AtCHX20 were consistently more sensitive on media containing 100 mM $Na^+$ or 500 mM $K^+$ at various pH (FIG. 2A) than the mutant yeast harboring the vector alone. KTA40-2 mutants grew as well as AtCHX20 transformants on standard synthetic complete (SC) medium.

Figure 2B:
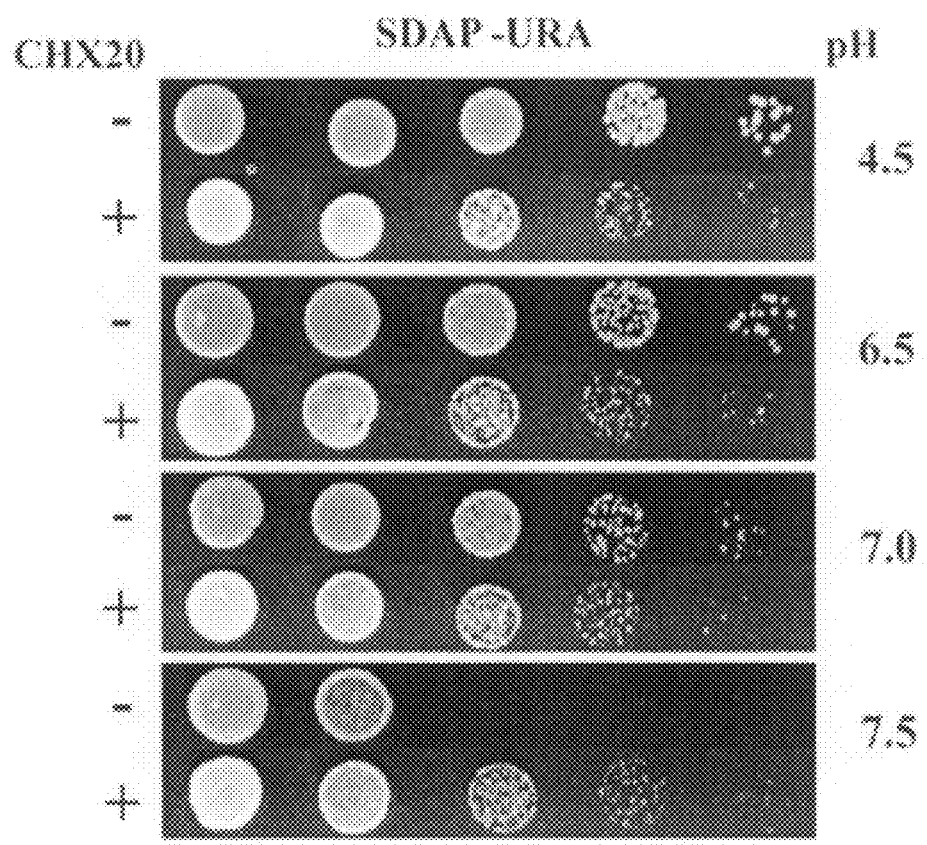

AtCHX20 enhanced KTA40-2 yeast mutant growth on slightly basic medium with no added $K^+$. At an external pH of 4.5 to 7.0, mutants grew relatively well with no added $K^+$. In fact, at acidic pH between 4.5 and 6.5, mutants grew consistently better than yeast transformants carrying AtCHX20. Curiously, growth of mutants carrying the vector alone was retarded at a pHext of 7.5, whereas transformants harboring AtCHX20 continued to grow as well as at pH 4.5 (FIG. 2B). Thus, strains carrying AtCHX20 had an advantage when the external pH was 7.5, suggesting that AtCHX20 conferred an ability to sustain growth at slightly basic pH.

Figure 2C:
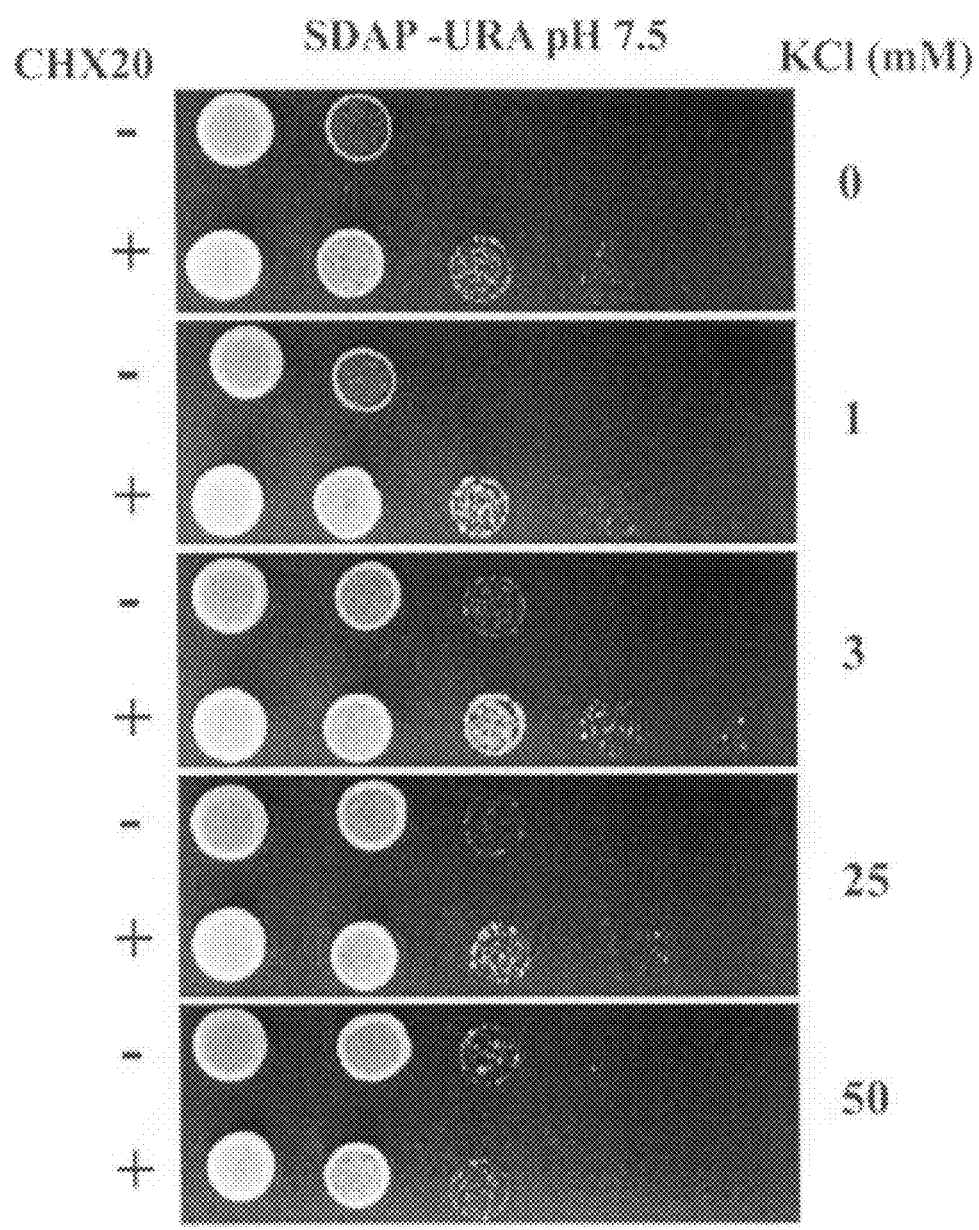

We tested the effect of external $K^+$ concentration on yeast growth at pH 7.5. Transformants harboring AtCHX20 consistently grew better than KTA40-2 mutants as long as the $K^+$ level was kept low, from approximately 0.4 to 3 mM (FIG. 2C). When no exogenous $K^+$ was added, the agar medium contained about 0.4 mM $K^+$. Increasing external KCl concentration beyond 25 mM decreased the beneficial effect of AtCHX20. Because $K^+$ is required to sustain growth of all cells, the enhanced growth of transformants at low $K^+$ levels suggests that AtCHX20 has a role in acquiring $K^+$ when the external pH is slightly alkaline, or in maintaining suitable cellular homeostasis for growth. This idea was confirmed by nearly similar growth exhibited by yeast mutants carrying either vector alone or AtCHX20 when $K^+$ is raised to 50 mM.

Figure 3A:
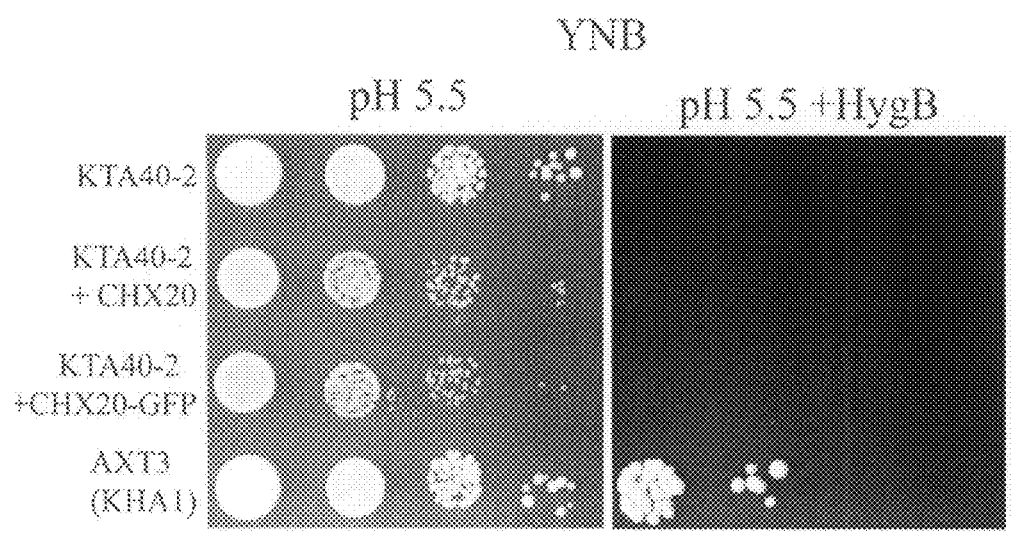
FIGS. 3A and 3B show that AtCHX20 fused to GFP is functionally active. KTA40-2 yeast (ena1-4Δ nha1Δ nhx1Δ kha1Δ) was transformed with empty pDR196 vector, AtCHX20, or CHX20-GFP. AXT3 (ena1-4Δ nha1Δ nhx1Δ) was transformed with empty vector and served as a native ScKHA1 positive control. Cells were serially diluted 10-fold and spotted on YNB plates.
Figure 3B:
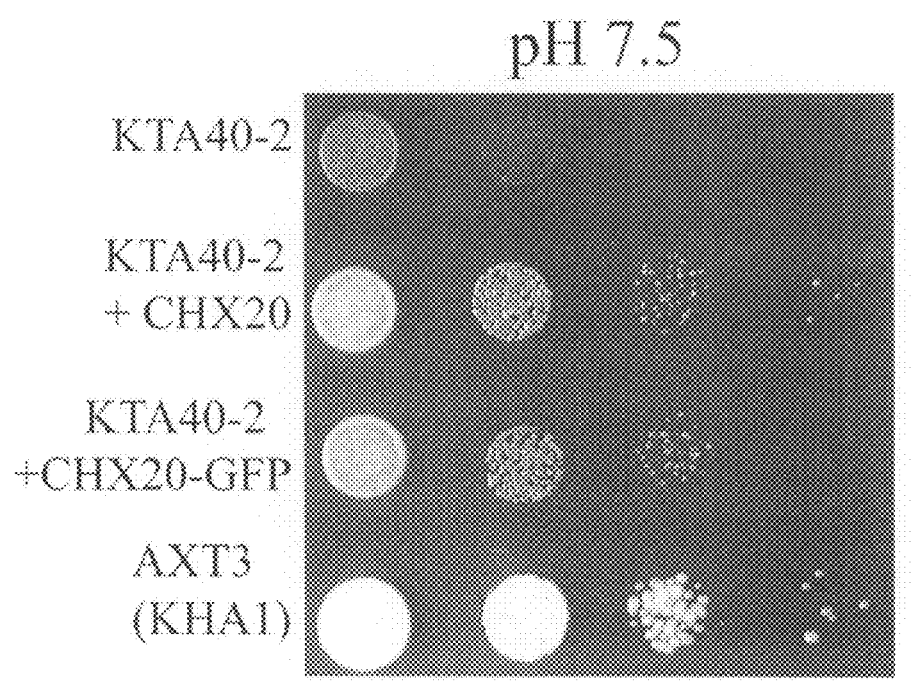

Yeast protein KHA1 was previously shown to confer tolerance to hygromycin (Maresova and Sychrova, 2005). The inventors here confirmed this in the AXT3 strain (FIG. 3A). The AXT3 strain has a functional wild-type KHA1 gene, but lacks three Na transporters (ena1-4Δ, nha1Δ, nhx1Δ). However, although transformants expressing AtCHX20 grew well at pH 5.5, they showed no growth in the presence of 150 mM hygromycin B. AtCHX20 did promote growth of mutants grown on yeast nitrogen base (YNB) medium at pH 7.5 similar to yeast KHA1 (FIG. 3B). These results mean that AtCHX20 and KHA1 likely share similar, but not identical, activities.

EXAMPLE 3

AtCHX20 is Preferentially Expressed in Guard Cells

Figure 4A:
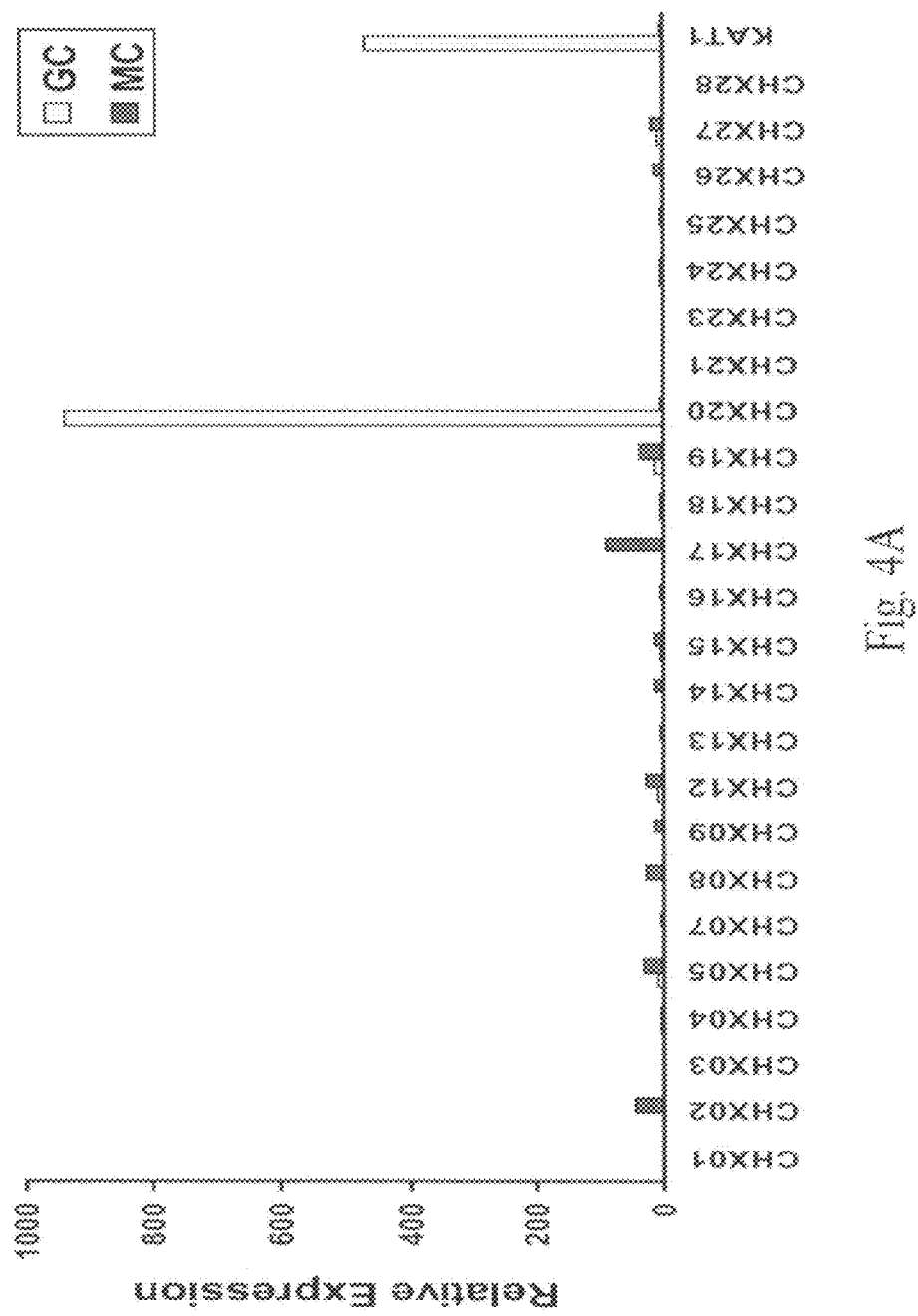
FIGS. 4A-B show AtCHX20 is preferentially expressed in guard cells.

Analyses of a guard cell transcriptome (Leonhardt et al., 2004; J. Kwak, N. Leonhardt, and J. I. Schroeder, unpublished data) revealed that only one member of the CHX gene family was highly expressed in guard cells. AtCHX20 showed little or no expression in mesophyll cells, whereas several other genes, such as CHX17, showed low to moderate expression (FIG. 4A). Furthermore, AtCHX20 expression is particularly strong in guard cells as shown by the 2-fold increase in normalized relative expression of AtCHX20 compared to that of AtKAT1, a $K^+$ channel preferentially expressed in guard cells (Nakamura et al., 1995).

Figure 4B:
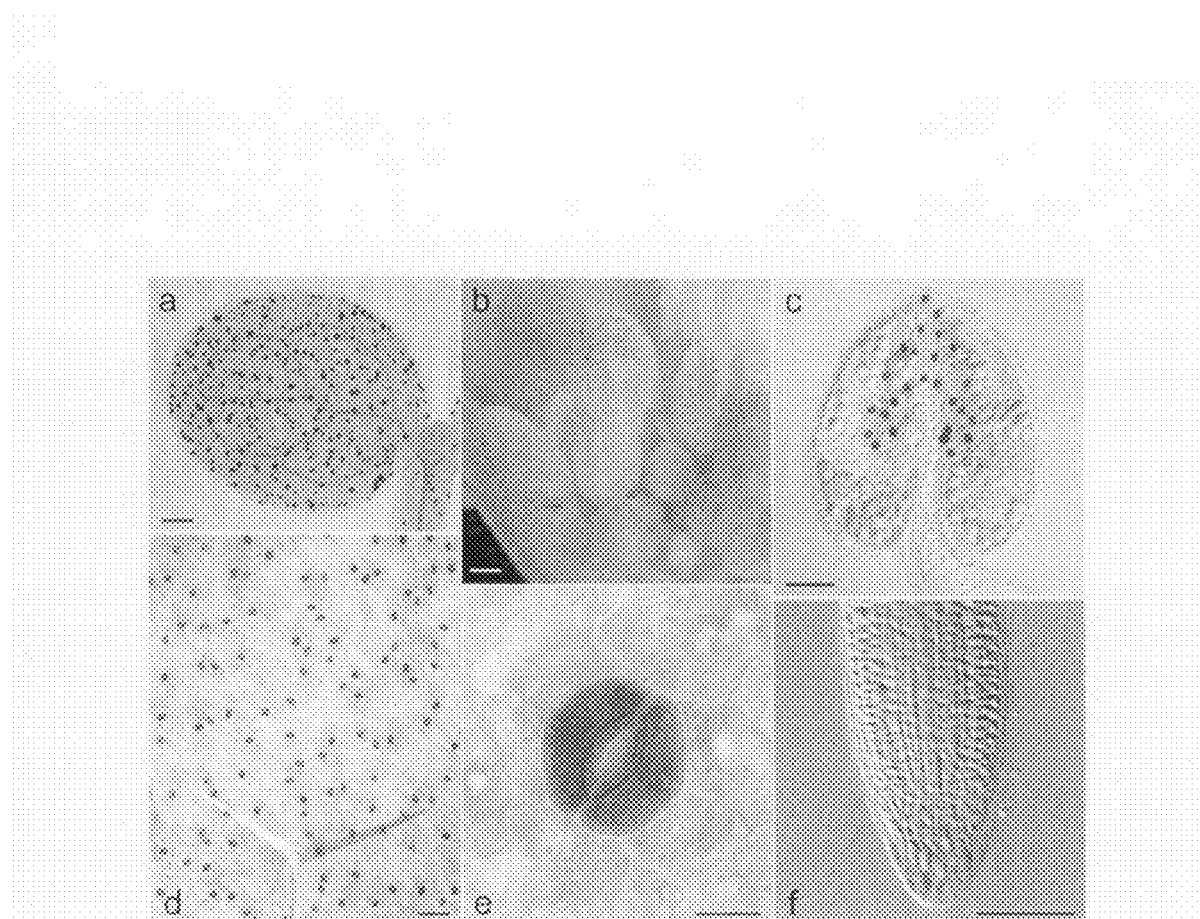

To verify the microarray results, AtCHX20 promoter driven GUS activity was determined. The AtCHX20 promoter has a sequence including bases 19,921,006 to 19,923,519 on chromosome 3 whose complete sequence is available from accession no. NC_003074.4 (SEQ ID NO: 39). The promoter drives expression of a gene encoding the amino acid sequence of NP_190940.1 (NCBI), Q9M353 (Uniprot) (SEQ ID NO: 36). Arabidopsis (Columbia [Col]) plants were transformed with a construct containing a 2-kb region upstream of the AtCHX20ORF transcriptionally fused to the GUS reporter gene. The 2 kb region comprises a substantial portion of the deduced AtCHX20 promoter sequence, and corresponds to bases 514-2514 of the deduced full-length promoter sequence (SEQ ID NO: 39). T2 seeds were collected from six independent transgenic lines and all six lines of CHX20TGUS analyzed gave similar expression patterns. Striking GUS activity was observed in guard cells located in expanded cotyledons and in hypocotyls of 1-week-old seedlings (FIG. 4B, photo a). Three-week-old rosette leaves (FIG. 4B, photos d and e) and cauline leaves also showed very high GUS staining in guard cells. However, GUS staining was not detected in leaf pavement epidermal cells or in mesophyll cells. Interestingly, GUS activity was also detected in guard cells of floral organs, including the sepal, anther (FIG. 4B, photos b and c), and carpel (data not shown). GUS activity was not detected in the differentiated cells of roots, although AtCHX20 expression was only observed in the root cap of 1-week-old seedlings (FIG. 4B, photo f), consistent with the microarray results of root cap cells (P. Benfey, personal communication). Thus, analyses of both AtCHX20 promoter-GUS expression and guard cell-specific transcriptome data clearly indicate selective expression of AtCHX20 in guard cells.

EXAMPLE 4

CHX20-GFP is Localized to Endomembranes

Figure 5A:
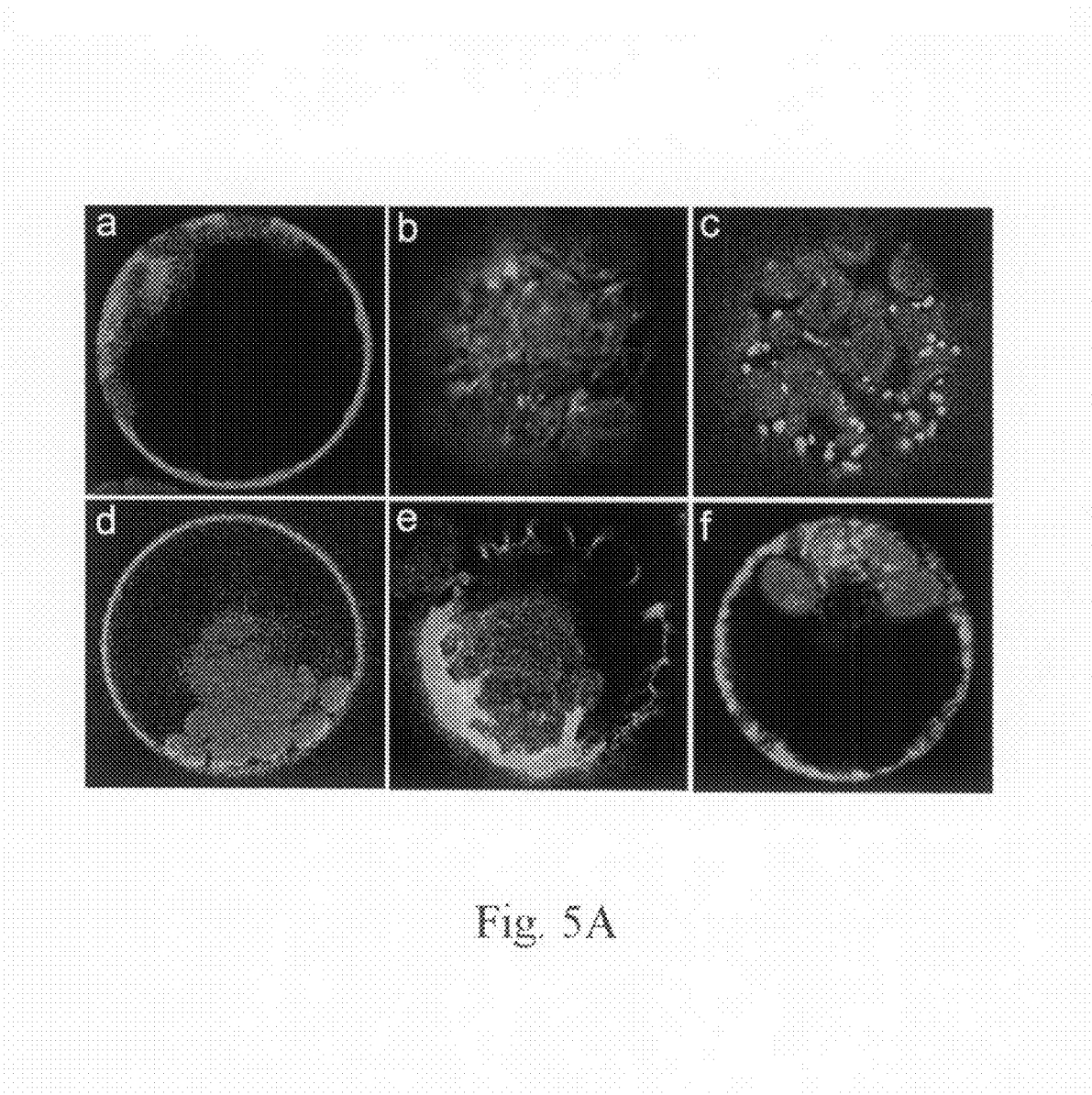
FIGS. 5A-C show endomembrane localization of AtCHX20-GFP protein. 5A, CHX20-GFP expression in *Arabidopsis* protoplast. Cauliflower mosaic virus 35S-driven GFP-tagged markers and AtCHX20-GFP (f) were transiently expressed in mesophyll protoplasts. Controls include free GFP (a); GFP tagged to HDEL (SEQ ID NO: 13) (b); ST-GFP (c); Ca21-dependent protein kinase9 (GFP-CPK9); d); and vacuolar water channel (GFP-d-TIP; e). Chloroplast autofluorescence is shown in red. 5B, Ara6-GFP and CHX20-GFP proteins show similar patterns of localization. CHX20-GFP (a-c) and Ara6 (d-f) are viewed at three optical planes from peripheral (a and d) to medial (c and f). Red emission is removed for clarity. Scale bar 5 10 mm. 5C, CHX20-GFP in guard cells. Transgenic *Arabidopsis* plants expressing control 35STpro-GFP (a) and 35STCHX20-GFP (b) are shown. Cells or leaves were observed under a laser confocal microscope. Scale bar=10 mm.

When transiently expressed in Arabidopsis mesophyll protoplasts, CHX20-GFP was visualized at the periphery of the nucleus and in the cytosol (FIG. 5A, photo f), suggesting that it is localized at the endoplasmic reticulum (ER) or in endomembranes. The CHX20-GFP signal was compared with those from a soluble GFP, GFP tagged to an ER retention sequence (GFPHDEL) (HDEL disclosed as SEQ ID NO: 13), or to markers such as sialyltransferase (ST)-GFP for trans-Golgi, GFP-CPK9 for PM, and GFP-dTIP for vacuolar membrane (FIG. 5A). Although CHX20-GFP appeared to be localized to endomembranes, its pattern did not coincide entirely with any of the markers tested. To determine its location more precisely, the CHX20-GFP and a Golgi marker, ST-red fluorescent protein constructs, were co-transfected into mesophyll protoplasts. Of the cells that coexpressed both probes, the pattern of green fluorescence-labeled structures for the most part did not overlap with that of the red fluorescence (data not shown), indicating that AtCHX20 is not restricted to the trans-Golgi membrane.

Stably transformed plants expressing cauliflower mosaic virus 35S-driven CHX20-GFP also showed perinuclear fluorescent signals in guard cells (FIG. 5C), whereas soluble free GFP appeared inside the nucleus. Strong fluorescent signals were also detected inside the cytoplasm of cells expressing CHX20-GFP relative to that expressing the free GFP control. Together, the results show that AtCHX20 is likely localized to a subpopulation of endomembranes, although the protein does not appear to be a fixed resident of either the ER, Golgi, vacuole, or PM.

Figure 5B:
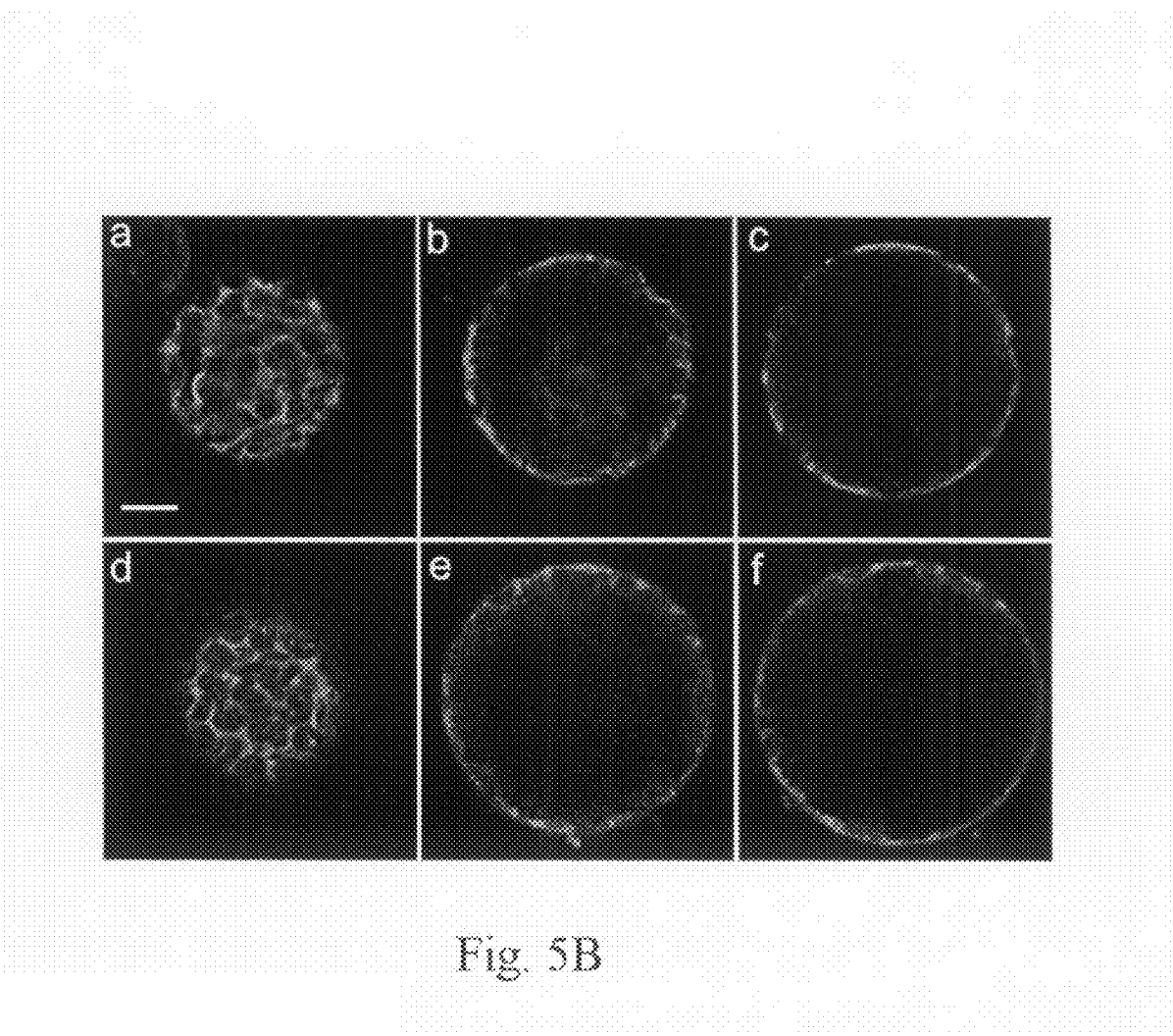
Figure 5C:
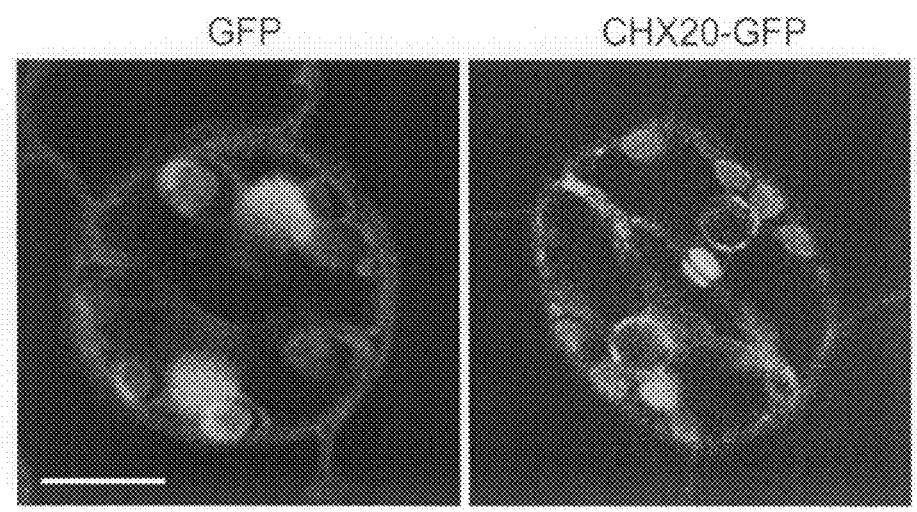

We have previously stated that AtCHX20 is associated with vesicles/membranes that traffic among various subcellular membranes (Jurgens, 2004). To verify this hypothesis, we examined the distribution of an endosome marker, Ara6-GFP (Ueda et al., 2001), and of AtCHX20 at several focal planes. Fluorescent signals of these two proteins were strikingly similar in several independent experiments. At the medial plane, the signal was cytoplasmic and at or near the PM (FIG. 5B). At the submedial focal plane, fluorescent signals were mostly cytoplasmic surrounding the plastids (FIG. 5B, data not shown). At the peripheral focal plane, the CHX20-GFP signal included several punctate regions. This pattern was distinct from a soluble ER marker that showed a reticulate pattern. The GFP-tagged CHX20 was functionally active as shown by its ability to restore growth of KTA40-2 yeast at alkaline pH (FIG. 3B). Ara6, a Rab5-related GTPase, is distributed on a subset of endosomes and is involved in regulating vesicular transport (Ueda et al., 2001). These results corroborate that an active AtCHX20 protein is associated with endosomal membranes.

EXAMPLE 5

Identification of chx20 Null Mutants

Figure 6A:
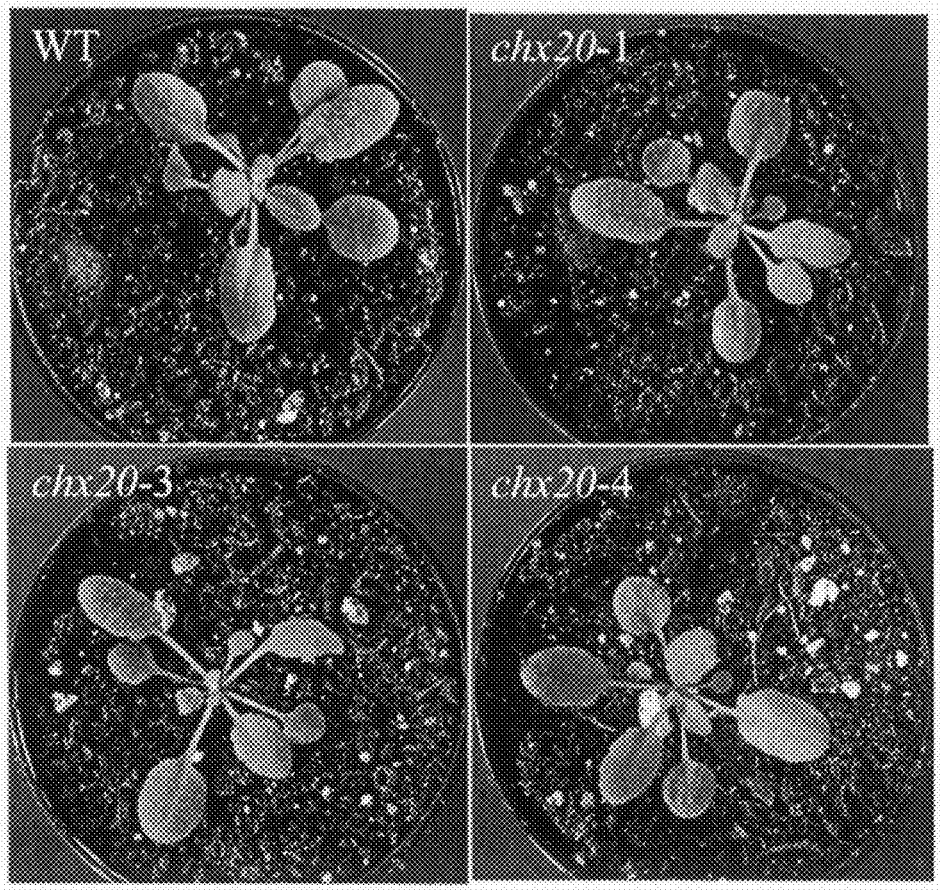
FIGS. 6A-B illustrate three alleles of T-DNA insertional chx20 mutants. 6A, Wildtype (WT) and mutant plants look similar. Sites of T-DNA insertion for chx20-1, chx20-3, and chx20-4 mutants are shown in FIG. 1A. 6B, Mutants lack AtCHX20 transcript. RNA isolated from leaves of chx20-1, chx20-3, and chx20-4 and wild type was reverse transcribed. The cDNA product was PCR amplified with primers F1 and R1, F2 and R2, and F3 and R2 shown in the genomic structure (top). Actin11 is amplified as a loading control.
Figure 6B:
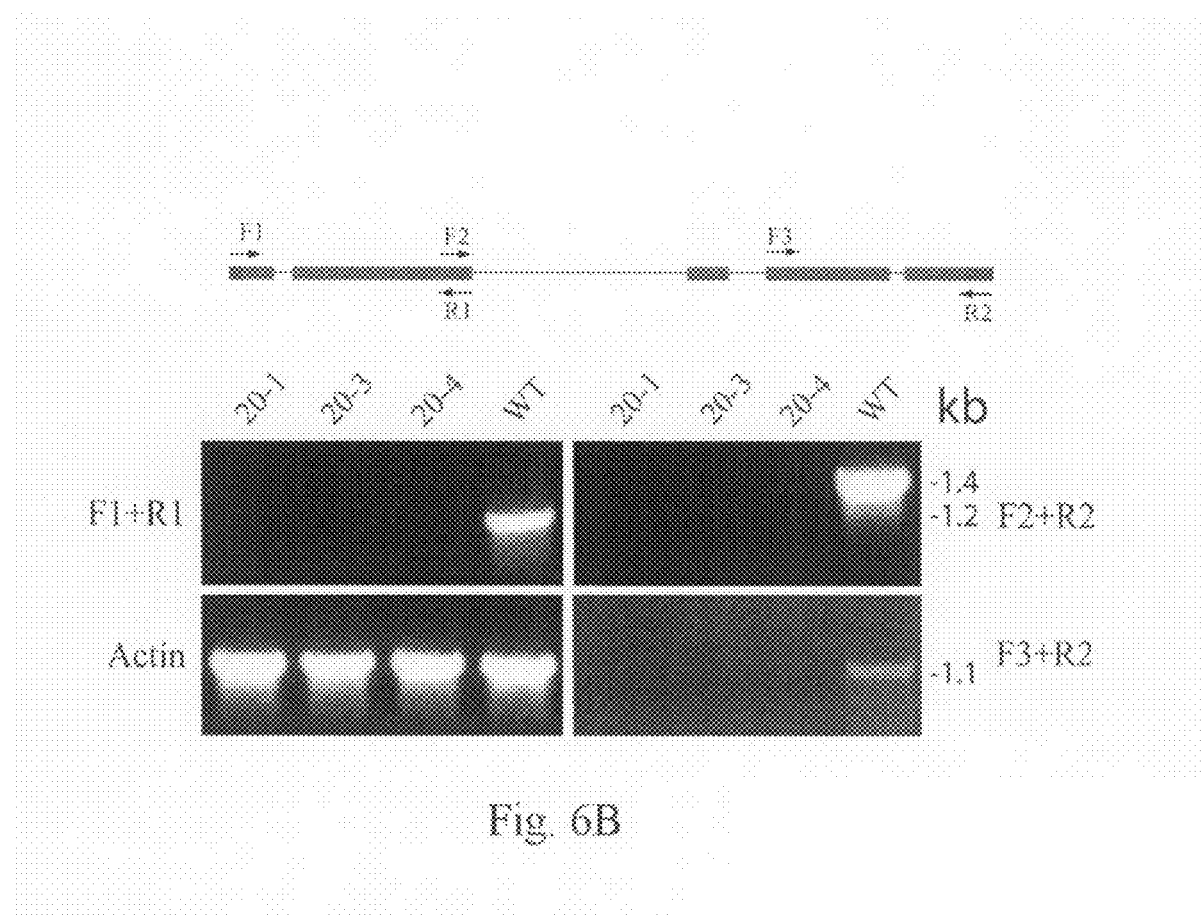

To determine the in-plant function of AtCHX20, we obtained three independent T-DNA insertional lines of *Arabidopsis* chx20. Two lines, chx20-1 and chx20-3, were identified in the SIGnAL database (Alonso et al., 2003), and one line, chx20-4, was obtained from Genoplante (France). To confirm the T-DNA insertion site and select homozygous lines, PCR-based screening was performed using CHX20-specific primers and T-DNA primers. Sequencing of the PCR-amplified fragments confirmed that a T-DNA insertion was located within exon 2 at coding sequence base 477 of the chx20-1 mutant, inside the third exon at the 1,299 coding sequence of chx20-3, and within the second intron of chx20-4 (FIG. 1A). The inventors tested for AtCHX20 transcripts in leaves of all the mutants. Reverse transcription (RT)-PCR was performed using AtCHX20 gene-specific primers located at either side of the T-DNA insertion using template cDNA reverse transcribed from total leaf RNA. No products were amplified, indicating an absence of messages in all three alleles (FIG. 6B). The AtCHX20 mutants showed no obvious morphological or growth differences compared to wild-type plants under standard growth conditions (FIG. 6A). Overall, the size and shape of the guard cells were indistinguishable between mutants and wild-type plants.

EXAMPLE 6

Impaired Stomatal Opening in chx20 Mutants

The highly specific expression of AtCHX20 in guard cells (FIG. 4) suggested that AtCHX20 plays a role in guard cell signaling and/or development. Because the inventors did not detect any developmental defects in the chx20 knockout mutants, they tested whether the chx20 null mutants had any altered stomatal movement.

First, a comparison of light-induced stomatal opening in mutants and wild-type plants was performed.

Figure 7A:
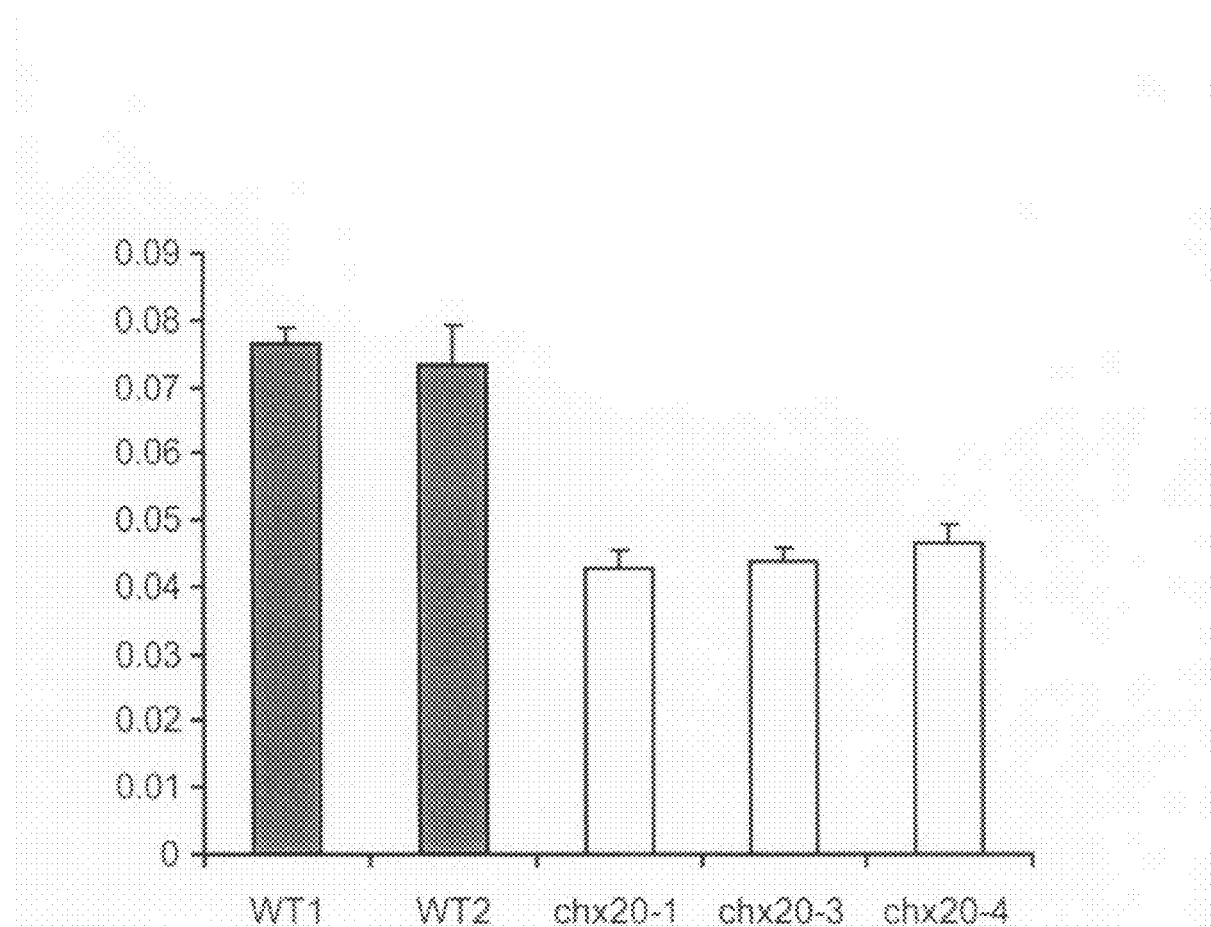
FIGS. 7A-C show that light-induced stomatal aperture was reduced in chx20 mutants. Aperture size is expressed as a ratio of maximal aperture size per length of guard cell (GC) pair. Twenty apertures were measured per treatment. Bar indicates SE. 7A, Three alleles show reduced stomatal opening. Excised leaves of dark-adapted wild type (WT1-2) and three mutants (chx20) were given 150 µE $m^{-2}$ $s^{-1}$ light or dark for 3 h. Leaves were placed in a solution containing 5 mM KCl and 10 mM MES-KOH at pH 6.15. Average light-enhanced pore size is shown from five independent experiments. 7B, Reduction in aperture size is independent of $K^+$ levels. Isolated epidermis from wild type and chx20-3 were incubated separately in 10 mM MES-Tris at pH 6.15 without $K^+$ at dark for 3 h. KCl was then added to 0.1, 1, or 10 mM, and the epidermal strips were irradiated for 3 h as in 7A. Results of dark (gray) and light (white) treatment are from one representative experiment of three. 7C, Effect of pH on stomatal opening. Isolated epidermis from wild type and chx20-3 were separately incubated 3 h in the dark in 5 mM KCl buffered to pH 6.15, 7.0, 7.5, or 8.0. Epidermal strips were exposed to light for 3 h. Average ratio of light-stimulated aperture/GC length of three independent experiments is shown.
Figure 7B:
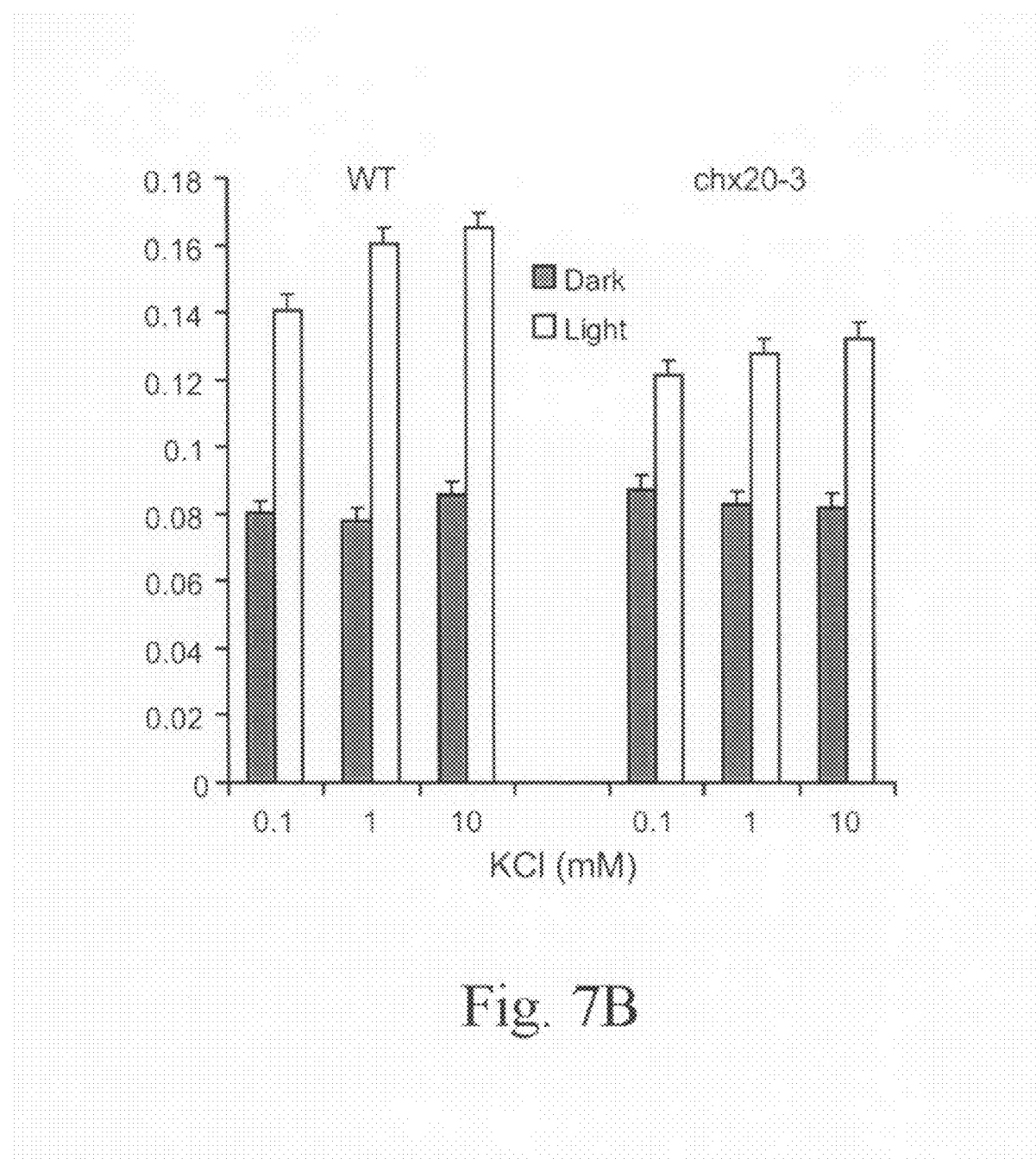

Excised leaves of chx20-1, chx20-3, and chx20-4 mutants were first exposed to white light for 3 h in a solution containing 5 mM KCl and 10 mM MES at pH 6.15. In all three mutants, the stomata failed to open as widely as wild-type plants. The ratio of light-induced stomatal opening per guard cell length in wild-type plants and in mutants ranged from 0.072 to 0.076 and 0.042 to 0.047, respectively. Thus, stomatal opening was reduced by approximately 35% in chx20 mutants (FIG. 7A). The external KCl concentration was reduced in the opening solution to 0.1 and 1.0 mM. The aperture size was reduced slightly in wild-type and mutant leaves exposed to 0.1 mM $K^+$ (FIG. 7B), implying that guard cell movement is limited at low $K^+$ concentration. However, chx20 mutants still showed approximately 35% reduction in light-induced stomatal opening regardless of the external $K^+$ concentration, indicating that the defect is not due to limited $K^+$ level alone.

Figure 7C:
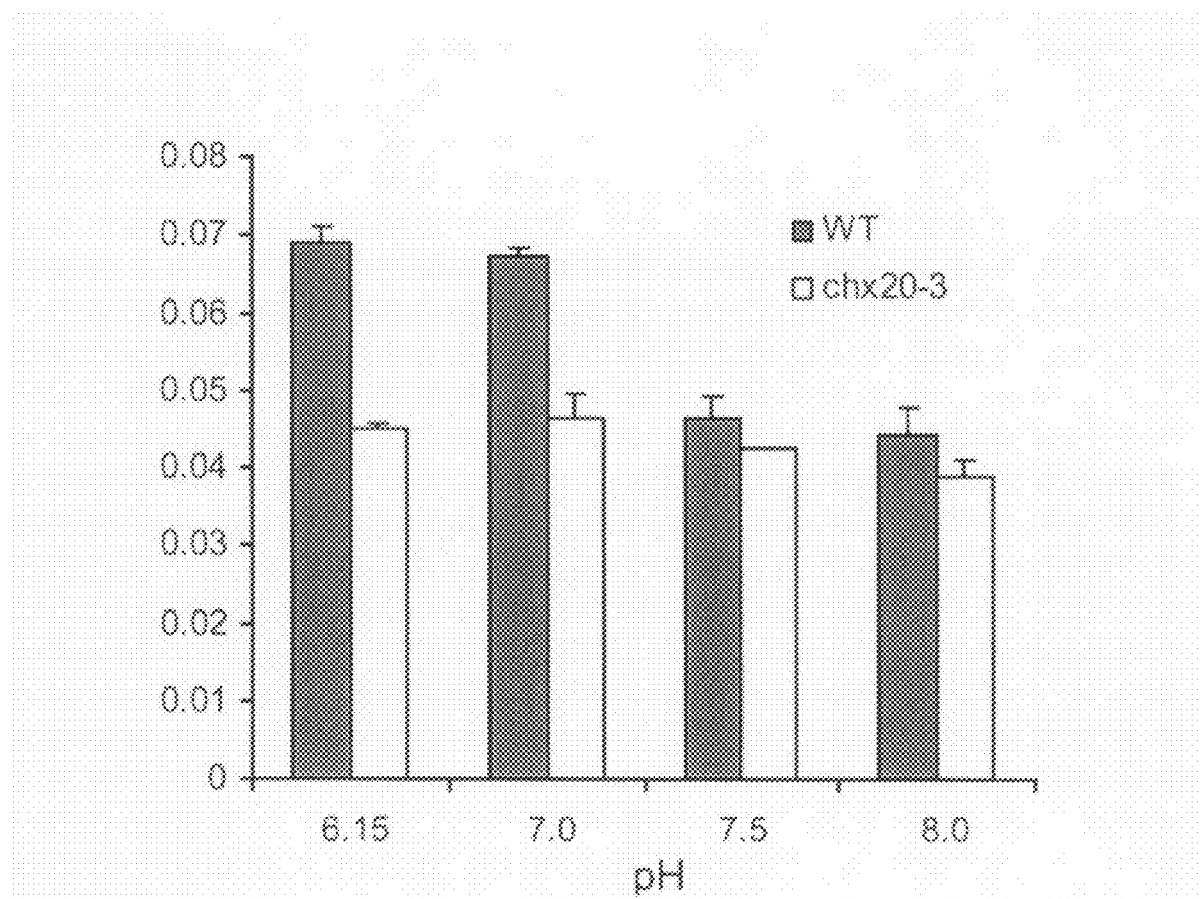

Using isolated epidermis, the inventors found that light induced stomatal opening was maximal at pH 6.1 and 7. At basic pH 7.5 and 8.0, light-induced opening was decreased in wild-type plants (FIG. 7C) consistent with inactivation by basic pH of inward-rectifying K+ channels and activation of outward-rectifying $K^+$ channels in *Vicia fava* guard cells (Ilan et al., 1994, 1996). However, mutants appeared to be insensitive to an acidic apoplastic pH that stimulated stomatal opening of wild-type guard cells. Thus, the reduced stomatal aperture of chx20 mutants was particularly apparent at pH 6.1 and 7.0. At pH 7.5 and 8.0, mutants showed reduced stomatal aperture nearly similar to that of wild type. Thus, chx20 mutants appeared to be unresponsive to pH regulation of guard cell movement.

To test whether stomatal closure was affected, isolated epidermis of wild-type and chx20 mutant leaves were first exposed to white light for 3 hours to induce stomatal opening and then incubated in 1 mM ABA to induce closure. The decrease in stomatal aperture was measured at 30-min intervals for 3 hours. Although the aperture size of wild-type plants was larger than that of mutants before ABA addition, the percentage of closure of wild type was higher than that of mutants at all times (FIG. 8). These results indicate that chx20 mutants were responsive to ABA; however, mutants were delayed in stomatal closure compared to wild-type plants (FIG. 8). These results mean that CHX20 can also participate in cellular events leading to stomatal closure.

The lack of a growth phenotype in yeast expressing AtCHX20 at pH 7.5 when $K^+_{ext}$ is replete teaches that other mechanisms take over to modulate $K^+$ and pH homeostasis when $K^+_{ext}$ is high (25-50 mM). Conceivably, high external $K^+$ could depolarize the cell membrane potential; increase $K^+$ influx into the cytosol and intracellular compartments, or both. With sufficient $K^+$ in the cell and intracellular compartments to support growth, the role of AtCHX20 may be shielded by other activities. Together, these results point to a role of AtCHX20 either in acquiring $K^+$ for cells under certain conditions and/or setting a suitable cellular pH homeostasis.

The inventors' genetic studies demonstrate that AtCHX20 participates in guard cell movement, although its role in mediating stomatal opening may involve multiple tasks. Based on functional studies of yeast in the present application, the inventors concluded that one role of AtCHX20 is to load guard cells with $K^+$. Stomatal aperture from chx20 mutants failed to fully open after light induction. If AtCHX20 has a major role in K+ loading, then the defect in opening might be minimized when $K^+_{ext}$ is not limiting. However, chx20 mutants were impaired in stomatal opening whether the $K^+_{ext}$ was at 0.1 or 10 mM, when $K^+$ entry and content in cells in theory are not limited. These results teach that AtCHX20 fills other roles.

The inventors then tested whether AtCHX20 activity was revealed at a different pH from that seen in KTA40-2 yeast. Stomatal opening was maximal at pH 6.0 to 7.0 and reduced at pH 7.5 to 8.0 in wild-type leaves, consistent with activation and deactivation by acidic pH of inward and outward $K^+$ channels, respectively, seen before (Ilan et al., 1994, 1996). Stomatal opening in mutants, however, failed to respond to acidic pH, suggesting that loss of AtCHX20 function could have interfered perhaps with pH homeostasis and with the activation and/or membrane trafficking of $K^+$ inward-rectifying channels.

Considering the large number of CPAs in plants (Maser et al., 2001; Pardo et al., 2006), it is surprising that single chx20 mutants were impaired in stomatal opening. The contribution of other CHXs appears to be minimal in guard cells; however, cation/$H^+$ antiporters, like NHXs, are highly expressed in shoots, roots (Yokoi et al., 2002), and guard cells (Shi and Zhu, 2002; J. M. Ward, unpublished data). Members of this family of plants (NHX1-NHX8) are localized to various membranes, including the vacuole, prevacuolar compartment, Golgi, or PM (Venema et al., 2003; Pardo et al., 2006). If other endomembrane $K^+$ ($Na^+$)/$H^+$ antiporters are unable to substitute for AtCHX20 function, then AtCHX20 occupies a distinct functional niche. It is therefore understood that AtCHX20 function differs from other cation/$H^+$ exchangers because of (1) differential endomembrane localization; (2) different substrate affinity and specificity (Km and Vmax); and (3) differential modulation by pH and/or other signals and different interacting partners.

Other Plant Species

Putative guard cell-specific genes were identified by the inventors in other plants by bioinformatics tools and are in the process of being experimentally confirmed. The likelihood that rice (*Oryza sativa*) OsCHX12 named Os05g02240 (TiGR) or Os05g0113300 is a functional homolog of AtCHX20 is quite high based on phylogenetic analysis conducted by the inventors (Sze H. et al. 2004). The inventors have also identified a homologous gene from a model legume plant, *Medicago truncatula*, or MtrDRAFT_AC148343g6v2, though the length of the promoter sequence is less certain and could vary from 678 to 2218 bp upstream from the initiation codon ATG.

The genes from poplar tree (*P. trichocarpa*) and from corn (*Zea mays*) represent available sequences that are putative AtCHX20 homologs.

From the foregoing experimental data, the inventors have determined that the guard cell-specific promoter of AtCHX20 (in *Arabidopsis thaliana*) is very likely conserved in all plants, and therefore would have the same or similar function as in *Arabidopsis*. As such it would be within one of ordinary skill, to prepare a vector containing the guard cell-specific promoter of AtCHX20 in the plant of interest and determine whether the promoter-driven activity of a candidate gene would cause increased stomatal opening or decreased opening.

With the promoter of the present invention, the inventors can create guard cell mutation in crops to allow them to withstand arid conditions. By regulating the size of stomatal pores, guard cells control $CO_2$ uptake for photosynthesis and transpirational water loss. In fact, more than 95% of plant water is lost through stomatal pores. During drought, plants close stomata in order to limit transpiration, which is mediated by abscisic acid (ABA).

Studies in *Arabidopsis* and other plant species have shown that transgenic expression of ABA biosynthetic enzymes and transcription activators or modified expression of ABA signaling elements could result in plants with improved drought tolerance. However, constitutive expression of ABA biosynthetic enzymes and overexpression of transcription activators could lead to unnecessary increases in cellular ABA and/or expression of undesired genes even under water sufficient conditions, which may bring about undesired traits to the plants.

The inventors found that effective genetic manipulation of drought hardiness can be achieved by the use of guard cell-specific promoters in manipulating cellular ABA levels, which will not affect other cells. This approach can efficiently contribute to improvement of water stress tolerance and a reduction in water consumption of plants. For example, guard cell-specific expression of "A" gene encoding positive regulators of ABA signaling, including an ABA receptor can be achieved by driving the target gene under the control of AtCHX20 promoter (or the homologous promoter in the crop), resulting in increase in the expression of "A" specifically in guard cells. Such a transgenic plant would respond more quickly to drought than control crops, reduce its stomatal aperture rapidly and efficiently, and so increase tolerance to drought.

Briefly, the procedure is as follows: (i) the AtCHX20 promoter is fused upstream of the gene of interest, and then the construct is subcloned into a suitable binary vector; (ii) the binary vector is introduced into the crop by *Agrobacterium*-mediated transformation; (iii) the transformed plant or cells are selected by antibiotic resistance and regenerated to yield fertile plants; and (iv) seeds carrying the transgene are collected.

Creating guard cell mutation in crops to allow them to withstand very wet conditions. Guard cell-specific expression of a gene of interest encoding negative regulators of ABA signaling can be achieved by driving the target gene under the control of AtCHX20 promoter (or the homologous promoter in the crop), resulting in increase in the expression of the gene of interest specifically in guard cells. This will lead to generation of crops plants which will maintain open stomata under water sufficient conditions, thus enabling the plant to withstand wet growth conditions. Moreover, the promoter of AtCHX20 and its related sequences in crops can be used to drive dsRNA-mediated silencing of genes specifically in guard cells.

Depending on the target genes (negative or positive regulators of ABA signaling), silencing a gene in a guard cell-specific manner will help to manipulate the regulation of stomatal apertures of the crop plants, which will contribute to optimizing their growth and production under different water conditions. The dsRNA sequence corresponds to the targeted gene to be silenced. Dicot crop or ornamental plants are transformed by *Agrobacterium*-mediated method. Crops like corn and rice can be transformed by biolistic bombardment of the suitable vector constructs to embryogenic cells, followed by regeneration of the cells to plantlets.

Having described the invention, many modifications thereto will become apparent to those skilled in the art to which it pertains without deviation from the spirit of the invention as defined by the scope of the appended claims.

LITERATURE CITED

Alonso J M, Stepanova A N, Leisse T J, Kim C J, Chen H M, Shinn P, Stevenson D K, Zimmerman J, Barajas P, Cheuk R, et al (2003) Genome wide insertional mutagenesis of *Arabidopsis thaliana*. Science 301:653-657.

Assmann S M (1993) Signal transduction in guard cells. Annu Rev Cell Biol 9: 345-375.

Bihler H, Eing C, Hebeisen S, Roller A, Czempinski K, Bertl A (2005) TPK1 is a vacuolar ion channel different from the slow-vacuolar cation channel. Plant Physiol 139: 417-424.

Blatt M R (2000) Cellular signaling and volume control in stomatal movements in plants. Annu Rev Cell Dev Biol 16: 221-241.

Cellier F, Conéjéro G, Ricaud L, Luu D T, Lepetit M, Gosti F, Casse F (2004) Characterization of AtCHX17, a member of the cation/H1 exchangers, CHX family, from *Arabidopsis thaliana* suggests a role in K1 homeostasis. Plant J 39: 834-846.

Clough S J, Bent A F (1998) Floral dip: a simplified method for *Agrobacterium*-mediated transformation of *Arabidopsis thaliana*. Plant J 16: 735-743.

De Angeli A, Monachello D, Ephritikhine G, Frachisse J M, Thomine S, Gambale F, Barbier-Brygoo H (2006) The nitrate/proton antiporter AtCLCa mediates nitrate accumulation in plant vacuoles. Nature 442: 939-942.

Dettmer J, Hong-Hermesdorf A, Stierhof Y D, Schumacher K (2006) Vacuolar H1-ATPase activity is required for endocytic and secretory trafficking in *Arabidopsis*. Plant Cell 18: 715-730.

Fan L M, Zhao Z, Assmann S M (2004) Guard cells: a dynamic signaling model. Curr Opin Plant Biol 7: 537-546.

Gao X Q, Li C G, Wei P C, Zhang X Y, Chen J, Wang X C (2005) The dynamic changes of tonoplasts in guard cells are important for stomatal movement in *Vicia faba*. Plant Physiol 139: 1207-1216.

Gietz D, Jean A S, Woods R A, Schiestl R H (1992) Improved method for high efficiency transformation of intact yeast. Nucleic Acids Res 20: 1425.

Guo F Q, Young J, Crawford N M (2003) The nitrate transporter AtNRT1.1 (CHL1) functions in stomatal opening and contributes to drought susceptibility in *Arabidopsis*. Plant Cell 15: 107-117.

Hall D, Evans A R, Newbury H J, Pritchard J (2006) Functional analysis of CHX21: a putative sodium transporter in *Arabidopsis*. J Exp Bot 57: 1201-1210.

Hawes C, Saint-Jore C, Martin B, Zheng H-Q (2001) ER confirmed as the location of mystery organelles in *Arabidopsis* plants expressing GFP. Trends Plant Sci 6: 245-246.

Homann U, Thiel G (2002) The number of K+ channels in the plasma membrane of guard cell protoplasts changes in parallel with the surface area. Proc Natl Acad Sci USA 99: 10215-10220.

Hosy E, Vavasseur A, Mouline K, Dreyer I, Gaymard F, Poree F, Boucherez J, Lebaudy A, Bouchez D, Very A A, et al (2003) The *Arabidopsis* outward K+ channel GORK is involved in regulation of stomatal movements and plant transpiration. Proc Natl Acad Sci USA 100: 5549-5554.

Ilan N, Schwartz A, Moran N (1994) External pH effects on the depolarization activated K+ channels in guard cell protoplasts of *Vicia faba*. J Gen Physiol 103: 807-831.

Ilan N, Schwartz A, Moran N (1996) External protons enhance the activity of the hyperpolarization-activated K+ channels in guard cell protoplasts of *Vicia faba*. J Membr Biol 154: 169-181.

Jurgens G (2004) Membrane trafficking in plants. Annu Rev Cell Dev Biol 20: 481-504.

Kane P M (2006) The where, when and how of organelle acidification by the yeast vacuolar H1-ATPase. Microbiol. Mol Biol Rev 70: 177-191.

Karimi M, Inze D, Depicker A (2002) GATEWAY vectors for *Agrobacterium* mediated plant transformation. Trends Plant Sci 7: 193-195.

Klein M, Perfus-Barbeoch L, Frelet A, Gaedeke N, Reinhardt D, Mueller-Roeber B, Martinoia E, Forestier C (2003) The plant multidrug resistance ABC transporter AtMRP5 is involved in guard cell hormonal signaling and water use. Plant J 33: 119-129.

Kovtun Y, Chiu W-L, Tena G, Sheen J (2000) Functional analysis of oxidative stress-activated MAPK cascade in plants. Proc Natl Acad Sci USA 97: 2940-2945.

Kwak J M, Murata Y, Baizabal-Aguirre V M, Merrill J, Wang M, Kemper A, Hawke S D, Tallman G, Schroeder J I (2001) Dominant negative guard cell K+ channel mutants reduce inward-rectifying K1 currents and light induced stomatal opening in *Arabidopsis*. Plant Physiol 127: 473-485.

Lee M H, Min M K, Lee Y J, Jin J B, Shin D H, Kim D H, Lee K-H, Hwang I (2002) ADP-ribosylation factor 1 of *Arabidopsis* plays a critical role in intracellular trafficking and maintenance of endoplasmic reticulum morphology in *Arabidopsis*. Plant Physiol 129: 1507-1520.

Leonhardt N, Kwak J M, Robert N, Waner D, Leonhardt G, Schroeder J I (2004) Microarray expression analyses of *Arabidopsis* guard cells and isolation of a recessive abscisic acid hypersensitive protein phosphatase 2C mutant. Plant Cell 16: 596-615.

Louget P, Coudret A, Couot-Gastelier J, Lasceve G (1990) Structure and ultrastructure of stomata. Biochem Physiol Pflanz 186: 273-279.

MacRobbie E A C (1999) Vesicle trafficking: a role in trans-tonoplast ion movements? J Exp Bot 50: 925-934.

Maresova L, Sychrova H (2005) Physiological characterization of *Saccharomyces cerevisiae* kha1 deletion mutants. Mol Microbiol 55: 588-600.

Maresova L, Sychrova H (2006) *Arabidopsis thaliana* CHX17 gene complements the kha1 deletion phenotypes in *Saccharomyces cerevisiae*. Yeast 16: 1167-1171.

Maser P, Thomine S, Schroeder J I, Ward J M, Hirschi K, Sze H, Talke I N, Antmann A, Maathius F L, Sanders D, et al (2001) Phylogenetic relationships within cation-transporter families of *Arabidopsis thaliana*. Plant Physiol 126: 1646-1667.

Meckel T, Hurst A C, Thiel G, Homann U (2004) Endocytosis against high turgor: intact guard cells of *Vicia faba* constitutively endocytose fluorescently labeled plasma membrane and GFP-tagged K+-channel KAT1. Plant J 39: 182-193.

Meckel T, Hurst A C, Thiel G, Homann U (2005) Guard cells undergo constitutive and pressure-driven membrane turnover. Protoplasma 226: 23-29.

Munn A L, Riezman H (1994) Endocytosis is required for the growth of vacuolar H1-ATPase-defective yeast: identification of six new END genes. J Cell Biol 127: 373-386.

Murashige T, Skoog F (1962) A revised medium for rapid growth and bioassays with tobacco tissue cultures. Physiol Plant 15: 473-497.

Nakamura R L, McKendree W L Jr, Hirsch R E, Sedbrook J C, Gaber R F, Sussman M R (1995) Expression of an *Arabidopsis* potassium channel gene in guard cells. Plant Physiol 109: 371-374.

Nelson H, Nelson N (1990) Disruption of genes encoding subunits of yeast vacuolar H1-ATPase causes conditional lethality. Proc Natl Acad Sci USA 87: 3503-3507.

Pardo J M, Cubero B, Leidi E O, Quintero F J (2006) Alkali cation exchangers: roles in cellular homeostasis and stress tolerance. J Exp Bot 57:1181-1199.

Paroutis P, Touret N, Grinstein S (2004) The pH of the secretory pathway: measurement, determinants and regulation. Physiology (Bethesda) 19:207-215.

Pei Z M, Ward J M, Schroeder J I (1999) Magnesium sensitizes slow vacuolar channels to physiological cytosolic calcium and inhibits fast vacuolar channels in fava bean guard cell vacuoles. Plant Physiol 121: 977-986.

Pratelli R, Sutter J U, Blatt M R (2004) A new catch in the SNARE. Trends Plant Sci 9: 187-195.

Quintero F J, Blatt M R, Pardo J M (2000) Functional conservation between yeast and plant endosomal Na+/H+ antiporters. FEBS Lett 471: 224-228.

Rea P A, Poole R J (1993) Vacuolar H1-translocating pyrophosphatase. Annu Rev Plant Physiol Plant Mol Biol 44: 157-180.

Rodriguez-Navarro A (2000) Potassium transport in fungi and plants. Biochim Biophys Acta 1469: 1-30.

Roelfsema M R, Hedrich R (2005) In the light of stomatal opening: new insights into 'the Watergate'. New Phytol 167: 665-691.

Schroeder J I, Allen G J, Hugouvieux V, Kwak J M, Waner D (2001) Cell signal transduction. Annu Rev Plant Physiol Plant Mol Biol 52:627-658.

Shi H, Zhu J K (2002) Regulation of expression of the vacuolar Na+/H+ antiporter gene AtNHX1 by salt stress and abscisic acid. Plant Mol Biol 50: 543-550.

Song C P, Guo Y, Qiu Q, Lambert G, Galbraith D W, Jagendorf A, Zhu J K (2004) A probable Na+ (K+)/H+ exchanger on the chloroplast envelope functions in pH homeostasis and chloroplast development in *Arabidopsis thaliana*. Proc Natl Acad Sci USA 101: 10211-10216.

Sze H (1985) H+-translocating ATPase: advances using membrane vesicles. Annu Rev Plant Physiol 36: 175-208.

Sze H, Li X, Palmgren M G (1999) Energization of plant cell membrane $H^+$-pumping ATPase: regulation and biosynthesis. Plant Cell 11:677-689.

Sze H, Padmanaban S, Cellier F, Honys D, Cheng N H, Bock K W, Conejero G, Li X, Twell D, Ward J, et al (2004) Expression pattern of a novel gene family AtCHX highlights their potential roles in osmotic adjustment and K+ homeostasis in pollen biology. Plant Physiol 136: 2532-2547.

Ueda T, Yamaguchi M, Uchimiya H, Nakano A (2001) Ara6, a plant-unique novel type Rab GTPase, functions in the endocytic pathway of *Arabidopsis thaliana*. EMBO J. 20: 4730-4741.

Venema K, Belver A, Marin-Manzano M C, Rodriguez-Rosales M P, Donaire J P (2003) A novel intracellular K+/H+ antiporter related to Na+/H+ antiporters is important for K+ ion homeostasis in plants. J Biol Chem 278: 22453-22459.

Very A A, Sentenac H (2003) Molecular mechanisms and regulation of K+ transport in higher plants. Annu Rev Plant Biol 54: 575-603.

Ward J M, Schroeder J I (1994) Calcium-activated K1 channels and calcium induced calcium release by slow vacuolar ion channels in guard cell vacuoles implicated in the control of stomatal closure. Plant Cell 6:669-683.

Yokoi S, Quintero F J, Cubero B, Ruiz M T, Bressan R A, Hasegawa P M, Pardo J M (2002) Differential expression and function of *Arabidopsis thaliana* NHX Na+/H+ antiporters in the salt stress response. Plant J 30:529-539.

All references cited are hereby incorporated by reference herein as if set forth in the specification in their entirety.

---

SEQUENCE LISTING

```
<160> NUMBER OF SEQ ID NOS: 39

<210> SEQ ID NO 1
<211> LENGTH: 18
<212> TYPE: DNA
<213> ORGANISM: Arabidopsis thaliana
<220> FEATURE:
<221> NAME/KEY: CDS
<222> LOCATION: (1)..(18)

<400> SEQUENCE: 1 aaa cgc gct ttc gga atc                                            18
Lys Arg Ala Phe Gly Ile
  1               5

<210> SEQ ID NO 2
<211> LENGTH: 6
<212> TYPE: PRT
<213> ORGANISM: Arabidopsis thaliana

<400> SEQUENCE: 2

Lys Arg Ala Phe Gly Ile
  1               5

<210> SEQ ID NO 3
```

```
<211> LENGTH: 35
<212> TYPE: DNA
<213> ORGANISM: Arabidopsis thaliana
<220> FEATURE:
<221> NAME/KEY: CDS
<222> LOCATION: (18)..(35)

<400> SEQUENCE: 3
acaccacaat atatcct gca gtc gct gga att aca                                  35
                   Ala Val Ala Gly Ile Thr
                    1               5

<210> SEQ ID NO 4
<211> LENGTH: 6
<212> TYPE: PRT
<213> ORGANISM: Arabidopsis thaliana

<400> SEQUENCE: 4

Ala Val Ala Gly Ile Thr
 1               5

<210> SEQ ID NO 5
<211> LENGTH: 52
<212> TYPE: DNA
<213> ORGANISM: Arabidopsis thaliana
<220> FEATURE:
<221> NAME/KEY: CDS
<222> LOCATION: (1)..(18)

<400> SEQUENCE: 5 cac ggc cca gcc aat gtc tctctaacaa attgacgctt agacaactta ataa              52
His Gly Pro Ala Asn Val
 1               5

<210> SEQ ID NO 6
<211> LENGTH: 6
<212> TYPE: PRT
<213> ORGANISM: Arabidopsis thaliana

<400> SEQUENCE: 6

His Gly Pro Ala Asn Val
 1               5

<210> SEQ ID NO 7
<211> LENGTH: 19
<212> TYPE: DNA
<213> ORGANISM: Arabidopsis thaliana
<220> FEATURE:
<221> NAME/KEY: CDS
<222> LOCATION: (2)..(19)

<400> SEQUENCE: 7 c tcc ctc atc tct ctc gtc                                                  19
  Ser Leu Ile Ser Leu Val
   1               5

<210> SEQ ID NO 8
<211> LENGTH: 6
<212> TYPE: PRT
<213> ORGANISM: Arabidopsis thaliana

<400> SEQUENCE: 8

Ser Leu Ile Ser Leu Val
 1               5

<210> SEQ ID NO 9
<211> LENGTH: 49
<212> TYPE: DNA
```

-continued

<213> ORGANISM: Arabidopsis thaliana

<400> SEQUENCE: 9
gttgtataaa ttcaaattga tatatgccaa cgtaaaaatg agggcaatc    49

<210> SEQ ID NO 10
<211> LENGTH: 14
<212> TYPE: DNA
<213> ORGANISM: Arabidopsis thaliana

<400> SEQUENCE: 10
gctaggcagg cccg    14

<210> SEQ ID NO 11
<211> LENGTH: 842
<212> TYPE: PRT
<213> ORGANISM: Arabidopsis thaliana

<400> SEQUENCE: 11

```
Met Pro Phe Asn Ile Thr Ser Val Lys Thr Ser Asn Gly Val Trp
 1               5                  10                  15

Gln Gly Asp Asn Pro Leu Asn Phe Ala Phe Pro Leu Leu Ile Val Gln
                20                  25                  30

Thr Ala Leu Ile Ile Ala Val Ser Arg Phe Leu Ala Val Leu Phe Lys
        35                  40                  45

Pro Leu Arg Gln Pro Lys Val Ile Ala Glu Ile Val Gly Gly Ile Leu
    50                  55                  60

Leu Gly Pro Ser Ala Leu Gly Arg Asn Met Ala Tyr Met Asp Arg Ile
65                  70                  75                  80

Phe Pro Lys Trp Ser Met Pro Ile Leu Glu Ser Val Ala Ser Ile Gly
                85                  90                  95

Leu Leu Phe Phe Leu Phe Leu Val Gly Leu Glu Leu Asp Leu Ser Ser
            100                 105                 110

Ile Arg Arg Ser Gly Lys Arg Ala Phe Gly Ile Ala Val Ala Gly Ile
        115                 120                 125

Thr Leu Pro Phe Ile Ala Gly Val Gly Val Ala Phe Val Ile Arg Asn
    130                 135                 140

Thr Leu Tyr Thr Ala Ala Asp Lys Pro Gly Tyr Ala Glu Phe Leu Val
145                 150                 155                 160

Phe Met Gly Val Ala Leu Ser Ile Thr Ala Phe Pro Val Leu Ala Arg
                165                 170                 175

Ile Leu Ala Glu Leu Lys Leu Leu Thr Thr Gln Ile Gly Glu Thr Ala
            180                 185                 190

Met Ala Ala Ala Ala Phe Asn Asp Val Ala Ala Trp Ile Leu Leu Ala
        195                 200                 205

Leu Ala Val Ala Leu Ala Gly Asn Gly Gly Glu Gly Gly Glu Lys
    210                 215                 220

Lys Ser Pro Leu Val Ser Leu Trp Val Leu Leu Ser Gly Ala Gly Phe
225                 230                 235                 240

Val Val Phe Met Leu Val Val Ile Arg Pro Gly Met Lys Trp Val Ala
                245                 250                 255

Lys Arg Gly Ser Pro Glu Asn Asp Val Val Arg Glu Ser Tyr Val Cys
            260                 265                 270

Leu Thr Leu Ala Gly Val Met Val Ser Gly Phe Ala Thr Asp Leu Ile
        275                 280                 285

Gly Ile His Ser Ile Phe Gly Ala Phe Val Phe Gly Leu Thr Ile Pro
    290                 295                 300
```

```
Lys Asp Gly Glu Phe Gly Gln Arg Leu Ile Glu Arg Ile Glu Asp Phe
305                 310                 315                 320

Val Ser Gly Leu Leu Leu Pro Leu Tyr Phe Ala Thr Ser Gly Leu Lys
                325                 330                 335

Thr Asp Val Ala Lys Ile Arg Gly Ala Glu Ser Trp Gly Met Leu Gly
            340                 345                 350

Leu Val Val Val Thr Ala Cys Ala Gly Lys Ile Val Gly Thr Phe Val
        355                 360                 365

Val Ala Val Met Val Lys Val Pro Ala Arg Glu Ala Leu Thr Leu Gly
370                 375                 380

Phe Leu Met Asn Thr Lys Gly Leu Val Glu Leu Ile Val Leu Asn Ile
385                 390                 395                 400

Gly Lys Glu Lys Lys Val Leu Asn Asp Glu Thr Phe Ala Ile Leu Val
                405                 410                 415

Leu Met Ala Leu Phe Thr Thr Phe Ile Thr Thr Pro Thr Val Met Ala
            420                 425                 430

Ile Tyr Lys Pro Ala Arg Gly Thr His Arg Lys Leu Lys Asp Leu Ser
        435                 440                 445

Ala Ser Gln Asp Ser Thr Lys Glu Glu Leu Arg Ile Leu Ala Cys Leu
450                 455                 460

His Gly Pro Ala Asn Val Ser Ser Leu Ile Ser Leu Val Glu Ser Ile
465                 470                 475                 480

Arg Thr Thr Lys Ile Leu Arg Leu Lys Leu Phe Val Met His Leu Met
                485                 490                 495

Glu Leu Thr Glu Arg Ser Ser Ser Ile Ile Met Val Gln Arg Ala Arg
            500                 505                 510

Lys Asn Gly Leu Pro Phe Val His Arg Tyr Arg His Gly Glu Arg His
        515                 520                 525

Ser Asn Val Ile Gly Gly Phe Glu Ala Tyr Arg Gln Leu Gly Arg Val
530                 535                 540

Ala Val Arg Pro Ile Thr Ala Val Ser Pro Leu Pro Thr Met His Glu
545                 550                 555                 560

Asp Ile Cys His Met Ala Asp Thr Lys Arg Val Thr Met Ile Ile Leu
                565                 570                 575

Pro Phe His Lys Arg Trp Asn Ala Asp His Gly His Ser His His His
            580                 585                 590

Gln Asp Gly Gly Gly Asp Gly Asn Val Pro Glu Asn Val Gly His Gly
        595                 600                 605

Trp Arg Leu Val Asn Gln Arg Val Leu Lys Asn Ala Pro Cys Ser Val
610                 615                 620

Ala Val Leu Val Asp Arg Gly Leu Gly Ser Ile Glu Ala Gln Thr Leu
625                 630                 635                 640

Ser Leu Asp Gly Ser Asn Val Val Glu Arg Val Cys Val Ile Phe Phe
                645                 650                 655

Gly Gly Pro Asp Asp Arg Glu Ser Ile Glu Leu Gly Gly Arg Met Ala
            660                 665                 670

Glu His Pro Ala Val Lys Val Thr Val Ile Arg Phe Leu Val Arg Glu
        675                 680                 685

Thr Leu Arg Ser Thr Ala Val Thr Leu Arg Pro Ala Pro Ser Lys Gly
690                 695                 700

Lys Glu Lys Asn Tyr Ala Phe Leu Thr Thr Asn Val Asp Pro Glu Lys
705                 710                 715                 720

Glu Lys Glu Leu Asp Glu Gly Ala Leu Glu Asp Phe Lys Ser Lys Trp
```

```
                        725                 730                 735
Lys Glu Met Val Glu Tyr Lys Glu Lys Glu Pro Asn Asn Ile Ile Glu
                740                 745                 750

Glu Ile Leu Ser Ile Gly Gln Ser Lys Asp Phe Asp Leu Ile Val Val
            755                 760                 765

Gly Arg Gly Arg Ile Pro Ser Ala Glu Val Ala Ala Leu Ala Glu Arg
        770                 775                 780

Gln Ala Glu His Pro Glu Leu Gly Pro Ile Gly Asp Val Leu Ala Ser
785                 790                 795                 800

Ser Ile Asn His Ile Ile Pro Ser Ile Leu Val Val Gln Gln His Asn
                805                 810                 815

Lys Ala His Val Glu Asp Ile Thr Val Ser Lys Ile Val Ser Glu Ser
            820                 825                 830

Ser Leu Ser Ile Asn Gly Asp Thr Asn Val
        835                 840

<210> SEQ ID NO 12
<211> LENGTH: 873
<212> TYPE: PRT
<213> ORGANISM: Saccharomyces cerevisiae

<400> SEQUENCE: 12

Met Ala Asn Thr Val Gly Gly Ile Leu Ser Gly Val Asn Pro Phe His
 1               5                  10                  15

Tyr Asn Ser Ser Ser Pro Leu Thr Leu Phe Leu Phe Gln Ala Cys Leu
                20                  25                  30

Ile Leu Leu Val Cys Asn Leu Ile His Ile Pro Phe Ser Met Met Arg
            35                  40                  45

Gln Pro Lys Val Ile Ser Glu Val Ile Ser Gly Val Ile Leu Gly Pro
        50                  55                  60

Thr Ile Phe Gly Gln Ile Pro Asn Tyr Thr Asn Thr Ile Phe Pro Thr
 65                  70                  75                  80

Ser Ser Ile Pro Gly Leu Asn Leu Val Ala Asn Leu Gly Ile Ile Leu
                85                  90                  95

Phe Met Phe Phe Leu Gly Leu Glu Val Asp Ile Ala Phe Ile Lys Lys
            100                 105                 110

His Leu Lys Lys Ala Leu Val Ile Gly Ile Val Thr Leu Ala Val Pro
        115                 120                 125

Phe Gly Phe Gly Cys Leu Leu Ala Ile Pro Leu Phe His Thr Tyr Ala
    130                 135                 140

Asn Lys Thr Glu Gly Glu Arg His Ile Lys Phe Ser Val Phe Met Val
145                 150                 155                 160

Phe Ile Ala Val Ser Ile Ser Val Thr Ala Phe Pro Val Leu Cys Arg
                165                 170                 175

Ile Leu Asn Glu Leu Arg Leu Ile Lys Asp Arg Ala Gly Ile Val Val
            180                 185                 190

Leu Ala Ala Gly Ile Ile Asn Asp Ile Met Gly Trp Ile Leu Leu Ala
        195                 200                 205

Leu Ser Ile Ile Leu Ser Ser Ala Glu Gly Ser Pro Val Asn Thr Val
    210                 215                 220

Tyr Ile Leu Leu Ile Thr Phe Ala Trp Phe Leu Ile Tyr Phe Phe Pro
225                 230                 235                 240

Leu Lys Tyr Leu Leu Arg Trp Val Leu Ile Arg Thr His Glu Leu Asp
                245                 250                 255

Arg Ser Lys Pro Ser Pro Leu Ala Thr Met Cys Ile Leu Phe Ile Met
```

```
                260                 265                 270
Phe Ile Ser Ala Tyr Phe Thr Asp Ile Ile Gly Val His Pro Ile Phe
            275                 280                 285
Gly Ala Phe Ile Ala Gly Leu Val Val Pro Arg Asp Asp His Tyr Val
        290                 295                 300
Val Lys Leu Thr Glu Arg Met Glu Asp Ile Pro Asn Ile Val Phe Ile
305                 310                 315                 320
Pro Ile Tyr Phe Ala Val Ala Gly Leu Asn Val Asp Leu Thr Leu Leu
                325                 330                 335
Asn Glu Gly Arg Asp Trp Gly Tyr Val Phe Ala Thr Ile Gly Ile Ala
            340                 345                 350
Ile Phe Thr Lys Ile Ile Ser Gly Thr Leu Thr Ala Lys Leu Thr Gly
        355                 360                 365
Leu Phe Trp Arg Glu Ala Thr Ala Ala Gly Val Leu Met Ser Cys Lys
370                 375                 380
Gly Ile Val Glu Ile Val Val Leu Thr Val Gly Leu Asn Ala Gly Ile
385                 390                 395                 400
Ile Ser Arg Lys Ile Phe Gly Met Phe Val Leu Met Ala Leu Val Ser
                405                 410                 415
Thr Phe Val Thr Thr Pro Leu Thr Gln Leu Val Tyr Pro Asp Ser Tyr
            420                 425                 430
Arg Asp Gly Val Arg Lys Ser Leu Ser Thr Pro Ala Glu Asp Asp Gly
        435                 440                 445
Ala Ala Asp Gly Leu Asp Ser Glu Gly Val Asp Lys Thr Glu Ile Asn
450                 455                 460
Thr Gln Leu Asn Ser Leu Ala Asp Val Ser Lys Tyr Arg Ile Gly Glu
465                 470                 475                 480
Leu Thr Thr Val Ile Asn Thr Thr Glu Ala Ile Ser Pro Ser Leu Lys
                485                 490                 495
Leu Leu Asn Tyr Leu Ser Leu Gly Val Ser Pro Lys Pro Lys Asn Asn
                500                 505                 510
Lys His Lys Asn Glu Thr Ser Leu Ser Arg Met Thr Thr Ala Thr Asp
        515                 520                 525
Ser Thr Leu Lys Ser Asn Thr Phe Lys Ile Lys Lys Met Val His Ile
    530                 535                 540
Trp Ser Lys Ser Val Asp Asp Val Asp Thr Asn Leu Ser Val Ile Asp
545                 550                 555                 560
Glu Lys Leu Thr Pro Phe Glu Gly Val Gly Ala Leu Arg Ala Ile His
                565                 570                 575
Leu Arg Leu Leu Thr Glu Arg Thr Thr Asp Leu Leu Gln Ser Ser Ser
            580                 585                 590
Leu Tyr Asn Asp Asp Pro His Phe Thr Ala Asn Thr Asp Ser Leu Leu
        595                 600                 605
Gln Ile Phe Asp Ile Phe Ser Asn Leu Ser Lys Ile Pro Phe Ser Ser
    610                 615                 620
Glu Val Ile Phe Ser Thr Met Arg Glu Lys Ala Ala Asn Ile Ala Thr
625                 630                 635                 640
Met Lys Met Asp Ser Thr Asp Leu Ile Leu Leu Pro Leu Lys Gly Ala
                645                 650                 655
Ser Tyr Glu Tyr Arg Gly Ser Pro Val Phe Ile Asp Glu Lys Tyr Ala
            660                 665                 670
Asn Phe Asp His Ile Tyr Ser His Leu Leu Gly Leu Asn Glu Leu Ser
        675                 680                 685
```

-continued

| | | | | | | | | | | | | | | | |
|---|---|---|---|---|---|---|---|---|---|---|---|---|---|---|---|
|Ser|Thr|Phe|Phe|Lys|Ser|Ile|Phe|Gln|Ser|Leu|Lys|Ala|Asn|Phe|Ala|
| |690| | | |695| | | |700| | | | | | |

Val Gln Ile Ser Asn Thr Tyr Gly Arg Leu Asn Ala Asp Arg Phe Lys
705                 710                 715                 720

Arg Lys Arg Phe Asn Leu Leu Leu Pro Lys Pro Tyr Leu Thr Gln Ser
            725                 730                 735

Asp Tyr Leu Gly Leu Tyr Leu Leu Leu Ile Cys Tyr Arg Asp Gly
        740                 745                 750

Tyr Asn Asn Asp Asn Ala Ser Cys Ser Ile Phe Ile Asn Ser Lys Asn
            755                 760                 765

Ile Asp Phe Ala Lys Asp Leu Ser Thr Ala Phe Ala Glu His Asp Trp
    770                 775                 780

Leu Asn Glu Ser Thr Ile Lys Ile Val Asp Ile Pro Phe Glu Thr Lys
785                 790                 795                 800

Val Pro Glu Glu Ala Ile Glu Lys Pro Ser Phe Ile Glu Thr Val Leu
            805                 810                 815

Asp Val Gly Leu Ser Asp Thr Ala Leu Ala Asp Ile Glu Glu Thr Thr
        820                 825                 830

Phe Ile Ile Gly Glu Asp Leu Pro Asp Glu Ser Glu Pro Phe Ser Glu
    835                 840                 845

Glu Val Arg Thr Val Ile Phe Glu Gly Ser Asn Arg Arg Phe Asp Thr
850                 855                 860

Leu Ile Val His His Phe Ser Ser Glu
865                 870

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Asp Glu Leu
  1

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgcgtcgaca ctctctacct agaacagttc gctgtac                            37

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgcggatcct ttggggattt caaaggactc tcttat                             36

<210> SEQ ID NO 16
<211> LENGTH: 53
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 16
ggggacaagt ttgtacaaaa aagcaggctc gtcgataaga gagtcctttg aaa              53

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggggaccact ttgtacaaga aagctgggtc tccgttaata cttagagaag actc             54

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtgatccgta acactctcta                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtcagcgatt gattgaacga                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtccatccga accaccaaga                                                   20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tggttcacgt agtgggccat cg                                                22

<210> SEQ ID NO 22
<211> LENGTH: 28
<212> TYPE: DNA
<213> ORGANISM: Artificial Sequence
<220> FEATURE:
```

<223> OTHER INFORMATION: Description of Artificial Sequence: Synthetic
       primer

<400> SEQUENCE: 22
gacactaacg gactcttttt ctctccac                                              28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 23
gagagtcctt tgaaatcccc aaaatgcc                                              28

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 24
atagttcttc tccttgcctt tagacggtg                                             29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 25
tgtttacgta atcgtcactt actgatcca                                             29

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 26
actataccga aagatggaga gtttg                                                 25

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 27
aaattgcaac cgtgtccatc agtc                                                  24

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
       primer -continued <210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29 cttttctcc ttgcctatgt tgagtacaat gagctccact aaacctta                49

<210> SEQ ID NO 30
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
taaaggttta gtggagctca ttgtactcaa cataggcaag gagaaaaag              49

<210> SEQ ID NO 31
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccatgcatta agccgaagtt taagtactag atcaatttat ttattgt                47

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tctctctcgt cgagtccatc cgaaccacca agatac                            36

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atggcagatg gtgaagacat tcag                                         24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaagcacttc ctgtggacta ttga                                              24

<210> SEQ ID NO 35
<211> LENGTH: 2762
<212> TYPE: DNA
<213> ORGANISM: Arabidopsis thaliana

<400> SEQUENCE: 35
gaactatatc acatgttcca aatatagacg agaacaaaac aaaaaaaaaa agtcgtcgat     60
aagagagtcc tttgaaatcc ccaaaatgcc cttcaacata acctccgtga aaacctcatc   120
taacggagta tggcaaggcg acaatccttt aaacttcgct tttccgttac tcatcgtcca   180
aacggcgtta atcatcgccg tcagtcgctt cctcgccgtc ttattcaaac ctctccgtca   240
acccaaagtc atcgccgaga ttgtcggagg gatttttgtta ggaccatcgg ctttaggtag   300
aaacatggcg tacatggacc gtatatttcc gaaatggagt atgccgatac tcgaatccgt   360
cgcgagcata ggacttctct tcttcctctt cctcgtcggt ctagaactcg atttatcatc   420
gatccgacga agcggcaaac gcgctttcgg aatcgcagtc gctggaatta cactaccgtt   480
tatcgccggc gtcggagtcg cgtttgtgat ccgtaacact ctctacaccg ccgcggataa   540
accaggttac gccgagtttc tcgttttcat gggagtcgca ctctcgatca cagcttttcc   600
ggtacttgcg cgtattttag cagagctcaa gcttttaacg actcagatag gagaaaccgc   660
gatggctgca gccgctttta acgatgtagc cgcgtggatt ttactcgctt tagcggttgc   720
gttagcgggt aatggcggtg agggaggtgg agagaaaaag agtccgttag tgtcgttgtg   780
ggttttgtta tcgggcgctg ggtttgtggt ttttatgttg gttgtgatcc gacccggaat   840
gaaatgggtc gcgaaacgtg gatctcctga aaacgacgtc gtacgcgagt cttacgtgtg   900
tttgacgtta gccggtgtta tggttccggg tttcgcgacg gatttaattg ggattcattc   960
gattttggga gcgtttgttt tcggtttgac tataccgaaa gatggagagt ttggtcagcg  1020
attgattgaa cgaattgagg attttgtttc cggtttactc ttaccgcttt atttcgctac  1080
gagtggtttg aagactgacg tggctaagat tagaggagct gagtcgtggg ggatgttggg  1140
tcttgttgtt gttacggctt gtgccgggaa gatagtcgga acttttgttg tggcggtgat  1200
ggttaaagtt ccggcgagag aggcgttgac acttggtttc ttgatgaata ctaaaggttt  1260
agtggagctc attgtactca acataggcaa ggagaaaaag gtactaaacg acgagacgtt  1320
tgcaatacta gtgctaatgg cactcttcac aacgttcata acgacgccta ctgtaatggc  1380
catttacaag ccggcacgtg gcacccaccg caaactaaaa gacttgtcgg cgagccaaga  1440
ctccaccaag gaagagcttc gcatcctagc ctgcctccac ggcccagcca atgtctcctc  1500
cctcatctct ctcgtcgagt ccatccgaac caccaagata ctacggctaa agctgtttgt  1560
gatgcatctg atggaactaa cggaacggtc ttcgtcaatc ataatggtgc aaagagcccg  1620
taaaaacgga cttcctttcg ttcaccgtta ccgtcatggt gagcgtcaca gcaacgtcat  1680
aggaggcttc gaagcctatc gtcaactagg ccgggtcgca gtccggccca tcaccgcagt  1740
ctctccatta cccacaatgc acgaagacat ttgcccacatg gcagatacca agagggtcac  1800
aatgatcatt ttaccttttcc acaaacgatg aaacgctgat catggtcata gccaccacca  1860
ccaagacgga ggaggagatg gaaacgtacc ggaaaacgtt ggtcatggtt ggcgattggt  1920
taaccaaagg gttttgaaga atgcgccgtg ttcggtggcg gttcttgtag accgtggact  1980
tgggtccatt gaggcccaaa cttttgagctt agatgggtcg aatgtggttg aaagggtttg  2040
tgtgattttc tttggtgggc ctgatgaccg tgagtctata gagctcggcg ggagaatggc  2100

```
tgagcatccg gccgttaaag ttaccgttat taggttttg gtaagagaaa cgttgaggag  2160
taccgccgtc actttacgac cggcaccgtc taaaggcaag gagaagaact atgccttttt  2220
aacaaccaac gtggatccag aaaaagaaaa ggaattagac gaaggggcat tggaagactt  2280
caagagcaaa tggaaagaaa tggtggagta caaagaaaag gaaccaaaca acatcattga  2340
agaaatactg tcaataggac agagtaaaga ctttgatcta atagtggttg aagagggag  2400 gataccgtcg gccgaggtgg cggcattagc tgagcgtcaa gctgaacatc ctgagttagg  2460
tcctatcgga gacgtgctcg cctcttcgat caaccacatc attccatcaa tccttgtggt  2520
tcaacaacac aacaaagctc atgtagagga tattacggtt tccaaaattg ttagtgagtc  2580
ttctctaagt attaacggag acacaaatgt atgataacaa taataaaatt gatctagtac  2640
ttaaacttcg gcttaatgca tggttaaagt ggttagttga agatgtagtt tatctacaat  2700
atatagatag ctcttgagta agaattgtaa gatcgtctac atataaataa ccatgattgg  2760
gc                                                                 2762
```

<210> SEQ ID NO 36
<211> LENGTH: 842
<212> TYPE: PRT
<213> ORGANISM: Arabidopsis thaliana

<400> SEQUENCE: 36

```
Met Pro Phe Asn Ile Thr Ser Val Lys Thr Ser Asn Gly Val Trp
  1               5                  10                  15

Gln Gly Asp Asn Pro Leu Asn Phe Ala Phe Pro Leu Leu Ile Val Gln
                 20                  25                  30

Thr Ala Leu Ile Ile Ala Val Ser Arg Phe Leu Ala Val Leu Phe Lys
             35                  40                  45

Pro Leu Arg Gln Pro Lys Val Ile Ala Glu Ile Val Gly Gly Ile Leu
         50                  55                  60

Leu Gly Pro Ser Ala Leu Gly Arg Asn Met Ala Tyr Met Asp Arg Ile
 65                  70                  75                  80

Phe Pro Lys Trp Ser Met Pro Ile Leu Glu Ser Val Ala Ser Ile Gly
                 85                  90                  95

Leu Leu Phe Phe Leu Phe Leu Val Gly Leu Glu Leu Asp Leu Ser Ser
                100                 105                 110

Ile Arg Arg Ser Gly Lys Arg Ala Phe Gly Ile Ala Val Ala Gly Ile
            115                 120                 125

Thr Leu Pro Phe Ile Ala Gly Val Gly Val Ala Phe Val Ile Arg Asn
        130                 135                 140

Thr Leu Tyr Thr Ala Ala Asp Lys Pro Gly Tyr Ala Glu Phe Leu Val
145                 150                 155                 160

Phe Met Gly Val Ala Leu Ser Ile Thr Ala Phe Pro Val Leu Ala Arg
                165                 170                 175

Ile Leu Ala Glu Leu Lys Leu Leu Thr Thr Gln Ile Gly Glu Thr Ala
            180                 185                 190

Met Ala Ala Ala Phe Asn Asp Val Ala Ala Trp Ile Leu Leu Ala
        195                 200                 205

Leu Ala Val Ala Leu Ala Gly Asn Gly Gly Glu Gly Gly Glu Lys
        210                 215                 220

Lys Ser Pro Leu Val Ser Leu Trp Val Leu Ser Gly Ala Gly Phe
225                 230                 235                 240

Val Val Phe Met Leu Val Val Ile Arg Pro Gly Met Lys Trp Val Ala
                245                 250                 255
```

-continued

```
Lys Arg Gly Ser Pro Glu Asn Asp Val Val Arg Glu Ser Tyr Val Cys
            260                 265                 270

Leu Thr Leu Ala Gly Val Met Val Ser Gly Phe Ala Thr Asp Leu Ile
        275                 280                 285

Gly Ile His Ser Ile Phe Gly Ala Phe Val Phe Gly Leu Thr Ile Pro
    290                 295                 300

Lys Asp Gly Glu Phe Gly Gln Arg Leu Ile Glu Arg Ile Glu Asp Phe
305                 310                 315                 320

Val Ser Gly Leu Leu Pro Leu Tyr Phe Ala Thr Ser Gly Leu Lys
            325                 330                 335

Thr Asp Val Ala Lys Ile Arg Gly Ala Glu Ser Trp Gly Met Leu Gly
        340                 345                 350

Leu Val Val Val Thr Ala Cys Ala Gly Lys Ile Val Gly Thr Phe Val
        355                 360                 365

Val Ala Val Met Val Lys Val Pro Ala Arg Glu Ala Leu Thr Leu Gly
370                 375                 380

Phe Leu Met Asn Thr Lys Gly Leu Val Glu Leu Ile Val Leu Asn Ile
385                 390                 395                 400

Gly Lys Glu Lys Lys Val Leu Asn Asp Glu Thr Phe Ala Ile Leu Val
            405                 410                 415

Leu Met Ala Leu Phe Thr Thr Phe Ile Thr Thr Pro Thr Val Met Ala
        420                 425                 430

Ile Tyr Lys Pro Ala Arg Gly Thr His Arg Lys Leu Lys Asp Leu Ser
        435                 440                 445

Ala Ser Gln Asp Ser Thr Lys Glu Glu Leu Arg Ile Leu Ala Cys Leu
450                 455                 460

His Gly Pro Ala Asn Val Ser Ser Leu Ile Ser Leu Val Glu Ser Ile
465                 470                 475                 480

Arg Thr Thr Lys Ile Leu Arg Leu Lys Leu Phe Val Met His Leu Met
            485                 490                 495

Glu Leu Thr Glu Arg Ser Ser Ser Ile Ile Met Val Gln Arg Ala Arg
        500                 505                 510

Lys Asn Gly Leu Pro Phe Val His Arg Tyr Arg His Gly Glu Arg His
        515                 520                 525

Ser Asn Val Ile Gly Gly Phe Glu Ala Tyr Arg Gln Leu Gly Arg Val
530                 535                 540

Ala Val Arg Pro Ile Thr Ala Val Ser Pro Leu Pro Thr Met His Glu
545                 550                 555                 560

Asp Ile Cys His Met Ala Asp Thr Lys Arg Val Thr Met Ile Ile Leu
            565                 570                 575

Pro Phe His Lys Arg Trp Asn Ala Asp His Gly His Ser His His His
        580                 585                 590

Gln Asp Gly Gly Asp Gly Asn Val Pro Glu Asn Val Gly His Gly
        595                 600                 605

Trp Arg Leu Val Asn Gln Arg Val Leu Lys Asn Ala Pro Cys Ser Val
610                 615                 620

Ala Val Leu Val Asp Arg Gly Leu Gly Ser Ile Glu Ala Gln Thr Leu
625                 630                 635                 640

Ser Leu Asp Gly Ser Asn Val Val Glu Arg Val Cys Val Ile Phe Phe
            645                 650                 655

Gly Gly Pro Asp Asp Arg Glu Ser Ile Glu Leu Gly Gly Arg Met Ala
        660                 665                 670

Glu His Pro Ala Val Lys Val Thr Val Ile Arg Phe Leu Val Arg Glu
```

```
                675                 680                 685
Thr Leu Arg Ser Thr Ala Val Thr Leu Arg Pro Ala Pro Ser Lys Gly
        690                 695                 700
Lys Glu Lys Asn Tyr Ala Phe Leu Thr Thr Asn Val Asp Pro Glu Lys
705                 710                 715                 720
Glu Lys Glu Leu Asp Glu Gly Ala Leu Glu Asp Phe Lys Ser Lys Trp
                725                 730                 735
Lys Glu Met Val Glu Tyr Lys Glu Lys Glu Pro Asn Asn Ile Ile Glu
            740                 745                 750
Glu Ile Leu Ser Ile Gly Gln Ser Lys Asp Phe Asp Leu Ile Val Val
            755                 760                 765
Gly Arg Gly Arg Ile Pro Ser Ala Glu Val Ala Ala Leu Ala Glu Arg
        770                 775                 780
Gln Ala Glu His Pro Glu Leu Gly Pro Ile Gly Asp Val Leu Ala Ser
785                 790                 795                 800
Ser Ile Asn His Ile Ile Pro Ser Ile Leu Val Val Gln Gln His Asn
                805                 810                 815
Lys Ala His Val Glu Asp Ile Thr Val Ser Lys Ile Val Ser Glu Ser
            820                 825                 830
Ser Leu Ser Ile Asn Gly Asp Thr Asn Val
        835                 840

<210> SEQ ID NO 37
<211> LENGTH: 2515
<212> TYPE: DNA
<213> ORGANISM: Arabidopsis thaliana

<400> SEQUENCE: 37
atgcccttca acataaccctc cgtgaaaacc tcatctaacg gagtatggca aggcgacaat      60
cctttaaact tcgcttttcc gttactcatc gtccaaacgg cgttaatcat cgccgtcagt     120
cgcttcctcg ccgtcttatt caaacctctc cgtcaaccca agtcatcgc cgagattgtc      180
ggagggattt tgttaggacc atcggcttta ggtagaaaca tggcgtacat ggaccgtata     240
tttccgaaat ggagtatgcc gatactcgaa tccgtcgcga gcataggact tctcttcttc     300
ctcttcctcg tcggtctaga actcgattta tcatcgatcc gacgaagcgg caaacgcgct     360
ttcggaatcg cagtcgctgg aattacacta ccgtttatcg ccggcgtcgg agtcgcgttt     420
gtgatccgta acactctcta caccgccgcg gataaaccag gttacgccga gtttctcgtt     480
ttcatgggag tcgcactctc gatcacagct tttccggtac ttgcgcgtat tttagcagag     540
ctcaagcttt taacgactca gataggagaa accgcgatgg ctgcagccgc ttttaacgat     600
gtagccgcgt ggattttact cgctttagcg gttgcgttag cgggtaatgg cggtgaggga     660
ggtggagaga aaaagagtcc gttagtgtcg ttgtgggttt tgttatcggg cgctgggttt     720
gtggttttta tgttggttgt gatccgaccc ggaatgaaat gggtcgcgaa acgtggatct     780
cctgaaaacg acgtcgtacg cgagtcttac gtgtgtttga cgttagccgg tgttatggtt     840
tccggtttcg cgacggattt aattgggatt cattcgattt ttggagcgtt tgttttcggt     900
ttgactatac cgaaagatgg agagtttggt cagcgattga ttgaacgaat tgaggatttt     960
gtttccggtt tactcttacc gctttatttc gctacgagtg gtttgaagac tgacgtggct    1020
aagattagag gagctgagtc gtgggggatg ttgggtcttg ttgttgttac ggcttgtgcc    1080
gggaagatag tcgaactttt tgttgtggcg gtgatggtta agttccggc gagagaggcg    1140
ttgacacttg gtttcttgat gaatactaaa ggtttagtgg agctcattgt actcaacata    1200
```

-continued

```
ggcaaggaga aaaaggtact aaacgacgag acgtttgcaa tactagtgct aatggcactc    1260
ttcacaacgt tcataacgac gcctactgta atggccattt acaagccggc acgtggcacc    1320
caccgcaaac taaaagactt gtcggcgagc caagactcca ccaaggaaga gcttcgcatc    1380
ctagcctgcc tccacggccc agccaatgtc tcctccctca tctctctcgt cgagtccatc    1440
cgaaccacca agatactacg gctaaagctg tttgtgatgc atctgatgga actaacggaa    1500
cggtcttcgt caatcataat ggtgcaaaga gcccgtaaaa acggacttcc tttcgttcac    1560
cgttaccgtc atggtgagcg tcacagcaac gtcataggag gcttcgaagc ctatcgtcaa    1620
ctaggccggg tcgcagtccg gcccatcacc gcagtctctc cattacccac aatgcacgaa    1680
gacatttgcc acatggcaga taccaagagg gtcacaatga tcattttacc tttccacaaa    1740
cgatggaacg ctgatcatgg tcatagccac caccaccaag acggaggagg agatggaaac    1800
gtaccggaaa acgttggtca tggttggcga ttggttaacc aaagggtttt gaagaatgcg    1860
ccgtgttcgg tggcggttct tgtagaccgt ggacttgggt ccattgaggc ccaaactttg    1920
agcttagatg ggtcgaatgt ggttgaaagg gtttgtgtga ttttctttgg tgggcctgat    1980
gaccgtgagt ctatagagct cggcgggaga atggctgagc atccggccgt aaagttacc    2040 gttattaggt ttttggtaag agaaacgttg aggagtaccg ccgtcacttt acgaccggca    2100
ccgtctaaag gcaaggagaa gaactatgcc tttttaacaa ccaacgtgga tccagaaaaa    2160
gaaaaggaat tagacgaagg ggcattggaa gacttcaaga gcaaatggaa agaaatggtg    2220
gagtacaaag aaaaggaacc aaacaacatc attgaagaaa tactgtcaat aggacagagt    2280
aaagactttg atctaatagt ggttggaaga gggaggatac cgtcggccga ggtggcggca    2340
ttagctgagc gtcaagctga acatcctgag ttaggtccta tcggagacgt gctcgcctct    2400
tcgatcaacc acatcattcc atcaatcctt gtggttcaac aacacaacaa agctcatgta    2460
gaggatatta cggtttccaa aattgttagt gagtcttctc taagtattaa cggag         2515
```

<210> SEQ ID NO 38
<211> LENGTH: 838
<212> TYPE: PRT
<213> ORGANISM: Arabidopsis thaliana
<400> SEQUENCE: 38

```
Met Pro Phe Asn Ile Thr Ser Val Lys Thr Ser Ser Asn Gly Val Trp
 1               5                  10                  15

Gln Gly Asp Asn Pro Leu Asn Phe Ala Phe Pro Leu Leu Ile Val Gln
             20                  25                  30

Thr Ala Leu Ile Ile Ala Val Ser Arg Phe Leu Ala Val Leu Phe Lys
         35                  40                  45

Pro Leu Arg Gln Pro Lys Val Ile Ala Glu Ile Gly Gly Ile Leu
     50                  55                  60

Leu Gly Pro Ser Ala Leu Gly Arg Asn Met Ala Tyr Met Asp Arg Ile
 65                  70                  75                  80

Phe Pro Lys Trp Ser Met Pro Ile Leu Glu Ser Val Ala Ser Ile Gly
                 85                  90                  95

Leu Leu Phe Phe Leu Phe Leu Val Gly Leu Glu Leu Asp Leu Ser Ser
            100                 105                 110

Ile Arg Arg Ser Gly Lys Arg Ala Phe Gly Ile Ala Val Ala Gly Ile
        115                 120                 125

Thr Leu Pro Phe Ile Ala Gly Val Gly Val Ala Phe Val Ile Arg Asn
    130                 135                 140

Thr Leu Tyr Thr Ala Ala Asp Lys Pro Gly Tyr Ala Glu Phe Leu Val
```

```
            145                 150                 155                 160
Phe Met Gly Val Ala Leu Ser Ile Thr Ala Phe Pro Val Leu Ala Arg
                165                 170                 175
Ile Leu Ala Glu Leu Lys Leu Leu Thr Thr Gln Ile Gly Glu Thr Ala
                180                 185                 190
Met Ala Ala Ala Phe Asn Asp Val Ala Ala Trp Ile Leu Leu Ala
        195                 200                 205
Leu Ala Val Ala Leu Ala Gly Asn Gly Gly Glu Gly Gly Gly Glu Lys
    210                 215                 220
Lys Ser Pro Leu Val Ser Leu Trp Val Leu Ser Gly Ala Gly Phe
225                 230                 235                 240
Val Val Phe Met Leu Val Val Ile Arg Pro Gly Met Lys Trp Val Ala
                245                 250                 255
Lys Arg Gly Ser Pro Glu Asn Asp Val Val Arg Glu Ser Tyr Val Cys
                260                 265                 270
Leu Thr Leu Ala Gly Val Met Val Ser Gly Phe Ala Thr Asp Leu Ile
                275                 280                 285
Gly Ile His Ser Ile Phe Gly Ala Phe Val Phe Gly Leu Thr Ile Pro
        290                 295                 300
Lys Asp Gly Glu Phe Gly Gln Arg Leu Ile Glu Arg Ile Glu Asp Phe
305                 310                 315                 320
Val Ser Gly Leu Leu Leu Pro Leu Tyr Phe Ala Thr Ser Gly Leu Lys
                325                 330                 335
Thr Asp Val Ala Lys Ile Arg Gly Ala Glu Ser Trp Gly Met Leu Gly
                340                 345                 350
Leu Val Val Thr Ala Cys Ala Gly Lys Ile Val Gly Thr Phe Val
        355                 360                 365
Val Ala Val Met Val Lys Val Pro Ala Arg Glu Ala Leu Thr Leu Gly
    370                 375                 380
Phe Leu Met Asn Thr Lys Gly Leu Val Glu Leu Ile Val Leu Asn Ile
385                 390                 395                 400
Gly Lys Glu Lys Lys Val Leu Asn Asp Glu Thr Phe Ala Ile Leu Val
                405                 410                 415
Leu Met Ala Leu Phe Thr Thr Phe Ile Thr Thr Pro Thr Val Met Ala
                420                 425                 430
Ile Tyr Lys Pro Ala Arg Gly Thr His Arg Lys Leu Lys Asp Leu Ser
                435                 440                 445
Ala Ser Gln Asp Ser Thr Lys Glu Glu Leu Arg Ile Leu Ala Cys Leu
    450                 455                 460
His Gly Pro Ala Asn Val Ser Ser Leu Ile Ser Leu Val Glu Ser Ile
465                 470                 475                 480
Arg Thr Thr Lys Ile Leu Arg Leu Lys Leu Phe Val Met His Leu Met
                485                 490                 495
Glu Leu Thr Glu Arg Ser Ser Ile Ile Met Val Gln Arg Ala Arg
                500                 505                 510
Lys Asn Gly Leu Pro Phe Val His Arg Tyr Arg His Gly Glu Arg His
                515                 520                 525
Ser Asn Val Ile Gly Gly Phe Glu Ala Tyr Arg Gln Leu Gly Arg Val
    530                 535                 540
Ala Val Arg Pro Ile Thr Ala Val Ser Pro Leu Pro Thr Met His Glu
545                 550                 555                 560
Asp Ile Cys His Met Ala Asp Thr Lys Arg Val Thr Met Ile Ile Leu
                565                 570                 575
```

```
Pro Phe His Lys Arg Trp Asn Ala Asp His Gly His Ser His His His
                580                 585                 590
Gln Asp Gly Gly Asp Gly Asn Val Pro Glu Asn Val Gly His Gly
        595                 600                 605
Trp Arg Leu Val Asn Gln Arg Val Leu Lys Asn Ala Pro Cys Ser Val
    610                 615                 620
Ala Val Leu Val Asp Arg Gly Leu Gly Ser Ile Glu Ala Gln Thr Leu
625                 630                 635                 640
Ser Leu Asp Gly Ser Asn Val Val Glu Arg Val Cys Val Ile Phe Phe
                645                 650                 655
Gly Gly Pro Asp Asp Arg Glu Ser Ile Glu Leu Gly Gly Arg Met Ala
        660                 665                 670
Glu His Pro Ala Val Lys Val Thr Val Ile Arg Phe Leu Val Arg Glu
    675                 680                 685
Thr Leu Arg Ser Thr Ala Val Thr Leu Arg Pro Ala Pro Ser Lys Gly
690                 695                 700
Lys Glu Lys Asn Tyr Ala Phe Leu Thr Thr Asn Val Asp Pro Glu Lys
705                 710                 715                 720
Glu Lys Glu Leu Asp Glu Gly Ala Leu Glu Asp Phe Lys Ser Lys Trp
                725                 730                 735
Lys Glu Met Val Glu Tyr Lys Glu Lys Glu Pro Asn Asn Ile Ile Glu
        740                 745                 750
Glu Ile Leu Ser Ile Gly Gln Ser Lys Asp Phe Asp Leu Ile Val Val
    755                 760                 765
Gly Arg Gly Arg Ile Pro Ser Ala Glu Val Ala Ala Leu Ala Glu Arg
770                 775                 780
Gln Ala Glu His Pro Glu Leu Gly Pro Ile Gly Asp Val Leu Ala Ser
785                 790                 795                 800
Ser Ile Asn His Ile Ile Pro Ser Ile Leu Val Val Gln Gln His Asn
                805                 810                 815
Lys Ala His Val Glu Asp Ile Thr Val Ser Lys Ile Val Ser Glu Ser
        820                 825                 830
Ser Leu Ser Ile Asn Gly
        835

<210> SEQ ID NO 39
<211> LENGTH: 2514
<212> TYPE: DNA
<213> ORGANISM: Artificial Sequence
<220> FEATURE:
<223> OTHER INFORMATION: Description of Artificial Sequence: Synthetic
      primer sequence including base 19,921,006 to 19,923,519
      on chromosome 3 whose complete sequence is available
      from accession no. NC_003074.4

<400> SEQUENCE: 39
tttggggatt tcaaaggact ctcttatcga cgactttttt tttttgtttt gttctcgtct      60
atatttggaa catgtgatat agttcaagta tgaagaagat atgtgaagaa atttataggc     120
aaaaattata aatgtattgg tttgaagatt caaaaaagta attatgttgt tacttgtaat     180
tttggtgcat ctcacgtgtg actagacctt gagtggaagt atttggtttt tttttttttt     240
cttatgatat ttgttttttt agtagaaaat ttaaaaacca ttagattttg ggtgctataa     300
ttagaaacca tctatgtctt tgaattgttc atgtttacaa taaagtatag aaagtaaaaa     360
tctactcaaa aacaatttgt ggttgctata actcattctt atcagtttta tttcaagcaa     420
aactaataac ataaatttag tattgagaag aaaaaaagaa acaactcgtc tcacagacgg     480
```

```
aaattgcaaa ctaaaataag agtggcttat caccgaagca ggaatcatgt gagtcaaacg    540
tgggacgcga gagatgggcg ttgacaaatg ctgcgtcggc gtggatgggt tttacaagtg    600
caaccaaatt gacacgtatc tatgacttct catatattcc aaagtatttc gatataagtt    660
ggcaatattt tcattaaata gagctgttga tttttccaag aagtggtatc tcaattctgc    720
ttggtattta cgactttcct aactttttat ctagtttaga ttgttcgtca agtttgaaat    780
aaaactgttg ataatagcta tgactatcat atacagtatg aaaaaattaa gagttagatt    840
gtggcaaaga gacatctgaa attgtagaaa taaaggatct aaagcagtgg actgcctcga    900
agatgctata aattttgtaa tcacacttta tttcgaccat tcatggtta agtaattatg     960
tatgtttgtg gtttaagatt aatataatga tcacacggtt ttctattaga tgttttggag   1020
cgttagttac ttttgtgcat attatcttaa ggatctctca aatccgattg acgcgataaa   1080
aaggtcacca aaagttatag actcgaaatc catattttct gacctaccta atggtcgaaa   1140
tattagtcca agacacatat ccaatggaaa aaaacttatt taaattttt aagagaaact    1200
acgtcaatca tattactttt taaaagttta gatagtggga gaattcacaa gaatactgat   1260
tacaaaaaaa aaaaaaaaaa aaaaaaaaaa actgaaaatc acgaggcgat cgttatttca   1320
tttcccttc tatgaaatag atttggactt ttcatgaagg caagccaaaa gtgccaaaca    1380
agtggtcctc caaattttga ggaacagtta gttcaaaaca tagcaagttt ggtctcaccc   1440
atctttttt acattacagc tcaaagatag aacattaaaa aaaaaaagaa aaaaaaagat    1500
ttatagagaa gattcatgaa tctagctaga ctattgtacc ttaaattgca gctcaaagtc   1560
atattttgca tgttgatcag atatgtcata agagttatgt caaatacact tgttgtatct   1620
ctttgtagaa aataagattg ctaatcctaa taattttgtt gacaaaaaaa agaaagaaaa   1680
gaatacatcc tcaatttata aagacactat agctttgaca ttgacgactc acacgcccaa   1740
ataaggtcgg cagagtgaaa ttgtctgtga aatcatggtg ttttaagttg tactggaact   1800
tgtgtatgaa acagtctata gcaataataa tgaaaaagaa acaacacatt ttgctccata   1860
gcttttgtat ttgtgtaaat cggaaagaaa agtggtttat tattcatggt cgaaaaaatc   1920
agaaaaatgg gtcgattaga gaaaaaagta attttcagtg gctacagtat aagtacagcg   1980
aactgttcta ggtagagagt cccattatac aacaacaact cattataaaa tttgacttca   2040
gtaacgactg attgagaata tgttaatgta cactaaacta ttgacattga tgtaattgta   2100
tattttgta caattacgtt agtaatatgg cgattgcacc tgattggtga agaatctata   2160
ttctcttcca gttaccctac actagaattt ttcaatgaag ttatcacttg acataatcaa   2220
tttaaaaatt tgatttcgag acttcgacga taaattttgt tgggccacta caaaaggttt   2280
tactgagtgc tgactactta ttataatagg cccaaacaaa acatatatgt tgggccacta   2340
cattattagc caaaagattt tactgtaact tattatgagc ccatacggag catttcacag   2400
ggaaaattta actaaacgcg aaagtggcgt tacgattatt agaatgattt cgtaataaac   2460
agaggattag ttaaatcacg tttcgattac tgtatatgat taaaaattaa agtt         2514
```

The invention claimed is:

1. An isolated plant promoter consisting of the nucleic acid sequence of SEQ ID NO: 39.

2. An isolated promoter consisting of the 2000 bp nucleotide sequence located immediately 5' upstream of the open reading frame of the AtCHX20 gene in the genomic DNA sequence of chromosome 3 of *Arabidopsis thaliana*.

3. A vector comprising the promoter of claim 1.

4. A vector comprising the promoter of claim 2.

5. A recombinant, double-stranded DNA molecule comprising:
   a) the promoter of claim 1, and
   b) the DNA sequence of a gene of interest, wherein said DNA sequence is operatively linked to the promoter in sense orientation.

6. The DNA molecule according to claim 5, wherein the gene can be a fusion of two or more genes.

7. A transgenic plant comprising the promoter of claim 1.

8. A transgenic plant comprising the DNA molecule of claim 5.

9. The transgenic plant of claim 8, wherein the plant is *Arabidopsis thaliana*.

10. A method of expressing a gene and/or variants thereof in a guard cell of a plant, said method comprising transforming the plant with the recombinant DNA molecule of claim 5.

11. The method of claim 10, wherein said plant is selected from the group consisting of *Oryza sativa, Medicago truncatula, P. trichocarpa, Zea mays,* or *Arabidopsis thaliana*.

12. An expression cassette, comprising: a) the isolated promoter of claim 1, and b) a second nucleotide sequence, which is expressed in a cell of a plant or in plant tissues, wherein said second nucleotide sequence is ligated 3' downstream of the promoter.

13. The expression cassette of claim 12, wherein the second nucleotide sequence codes for green fluorescent protein (GFP).

14. A method of altering the stomatal opening in a plant, the method comprising:
  introducing into plant tissue a recombinant expression cassette comprising the plant promoter of claim 1 operably linked to the polynucleotide sequence of SEQ ID NO: 37;
  regenerating the plant tissue into a whole plant, whereby the regenerated plant transcribes the polynucleotide sequence; and
  selecting plants having altered stomatal opening.

15. The recombinant DNA molecule according to claim 5, wherein the DNA sequence of b) comprises the nucleotide sequence of SEQ ID NO: 37.

16. A transgenic plant cell transformed by the vector of claim 4.

17. The isolated plant promoter of claim 2, wherein the promoter activity is increased in guard cells of plant tissues selected from the group consisting of leaf, cotyledon, sepals, or anthers.

18. A recombinant, double-stranded DNA molecule comprising:
  a) the promoter of claim 2, and
  b) the DNA sequence of a gene of interest, wherein said DNA sequence is operatively linked to the promoter in sense orientation.

19. The DNA molecule according to claim 18, wherein the gene can be a fusion of two or more genes.

20. A transgenic plant comprising the promoter of claim 2.

21. A transgenic plant comprising the DNA molecule of claim 18.

22. The transgenic plant of claim 21, wherein the plant is *Arabidopsis thaliana*.

23. A method of expressing a gene and/or variants thereof in a guard cell of a plant, said method comprising transforming the plant with the recombinant DNA molecule of claim 18.

24. An expression cassette, comprising: a) the isolated promoter of claim 2, and b) a second nucleotide sequence, which is expressed in a cell of a plant or in plant tissues, wherein said second nucleotide sequence is ligated downstream of the promoter.

25. A method of altering the stomatal opening in a plant, the method comprising:
  introducing into plant tissue a recombinant expression cassette comprising the plant promoter of claim 2 operably linked to the polynucleotide sequence of SEQ ID NO: 37;
  regenerating the plant tissue into a whole plant, whereby the regenerated plant transcribes the polynucleotide sequence; and
  selecting plants having altered stomatal opening.

26. The recombinant DNA molecule according to claim 18, wherein the DNA sequence of b) comprises the nucleotide sequence of SEQ ID NO: 37.

* * * * *